United States Patent
Kamiya et al.

(10) Patent No.: US 9,242,928 B2
(45) Date of Patent: Jan. 26, 2016

(54) COMPOUND, KINESIN SPINDLE PROTEIN INHIBITOR, AND APPLICATION THEREOF

(71) Applicant: FUJITSU LIMITED, Kawasaki-shi, Kanagawa (JP)

(72) Inventors: Nozomu Kamiya, Yachiyo (JP); Atsushi Tomonaga, Musashino (JP); Hajime Sugiyama, Nakano (JP)

(73) Assignee: FUJITSU LIMITED, Kawasaki (JP)

( * ) Notice: Subject to any disclaimer, the term of this patent is extended or adjusted under 35 U.S.C. 154(b) by 293 days.

(21) Appl. No.: 13/901,282

(22) Filed: May 23, 2013

(65) Prior Publication Data
US 2013/0317110 A1 Nov. 28, 2013

Related U.S. Application Data

(63) Continuation of application No. PCT/JP2010/071656, filed on Dec. 3, 2010.

(51) Int. Cl.
| | | |
|---|---|---|
| A61K 31/165 | (2006.01) | |
| A61K 45/06 | (2006.01) | |
| C07C 237/06 | (2006.01) | |
| C07C 237/20 | (2006.01) | |

(52) U.S. Cl.
CPC .............. *C07C 237/20* (2013.01); *A61K 31/165* (2013.01); *A61K 45/06* (2013.01); *C07C 237/06* (2013.01); *C07C 2102/08* (2013.01)

(58) Field of Classification Search
CPC ..... A61K 31/165; A61K 45/06; C07C 237/06
USPC .............................. 514/620; 564/164; 435/375
See application file for complete search history.

(56) References Cited

U.S. PATENT DOCUMENTS

| | | | |
|---|---|---|---|
| 5,344,836 | A | 9/1994 | Hamanaka et al. |
| 6,121,240 | A | 9/2000 | Rosenberg et al. |
| 2004/0034232 | A1 | 2/2004 | Kontani et al. |
| 2008/0234281 | A1 | 9/2008 | Garbaccio et al. |
| 2008/0292626 | A1 | 11/2008 | Wang et al. |
| 2009/0118267 | A1 | 5/2009 | Finsinger et al. |
| 2012/0130147 | A1 | 5/2012 | Finsinger et al. |

FOREIGN PATENT DOCUMENTS

| | | |
|---|---|---|
| DE | 10 2005 010 000 A1 | 9/2006 |
| EP | 1 340 750 A1 | 9/2003 |
| JP | 6-72978 A | 3/1994 |
| WO | 2005/092011 A2 | 10/2005 |
| WO | 2008/147852 A1 | 12/2008 |

OTHER PUBLICATIONS

Blangy, A. et al., "Phosphorylation by p34cdc2 Regulates Spindle Association of Human Eg5, a Kinesin-Related Motor Essential for Bipolar Spindle Formation In Vivo", Cell, vol. 83, Dec. 29, 1995, pp. 1159-1169.
Ferhat, L. et al, "Expression of the Mitotic Motor Protein Eg5 in Postmitotic Neurons: Implications for Neuronal Development", The Journal of Neuroscience, vol. 18, No. 19, Oct. 1, 1998, pp. 7822-7835.
Vaultier, M. et al., "Synthesis of functional alpha-aminophosphonic esters from aziridines", Bulletin de la Societe Chimique de France, No. 7-8, Pt. 2, 1979, pp. 343-346.
International Search Report for PCT/JP2010/071656, mailing date of Feb. 8, 2011.
Coleman, P.J. et al., Inhibitors of the mitotic kinesin spindle protein, vol. 14, No. 12 (2004), p. 1659-1668.
Jiang, C. et al., Kinesin spindle protein Inhibitors as anticancer agents, vol. 16, No. 11 (2006), p. 1517-1532.
Pinkerton, A.B., Imidazole based kinesin spindle protein inhibitors, vol. 17, No. 7 (2007), p. 875-878.
Jiang, C. et al., Kinesin spindle protein inhibitors in cancer: a patent review (2008-present), vol. 23, No. 12 (Dec. 1, 2013), p. 1547-1560.
Extended European Search Report dated Aug. 10, 2015, issued in counterpart European Patent Application No. 10860393.7. (7 pages).

*Primary Examiner* — Raymond Henley, III
(74) *Attorney, Agent, or Firm* — Westerman, Hattori, Daniels & Adrian, LLP

(57) ABSTRACT

A compound represented by the following General Formula (I):

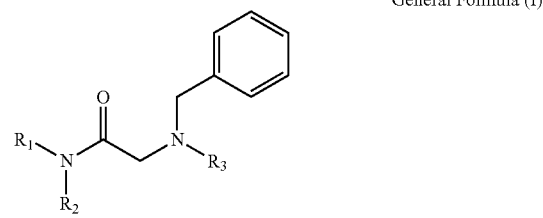

General Formula (I)

where, in General Formula (I),
$R_1$ and $R_2$ each represent an alkyl group which may have a substituent,
$R_3$ represents the following General Formula (II) or (III), and
$R_1$ and $R_2$ may be identical or different,

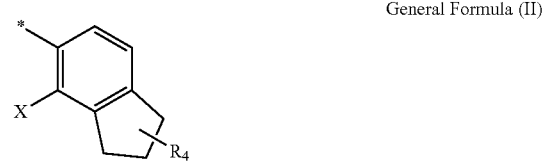

General Formula (II)

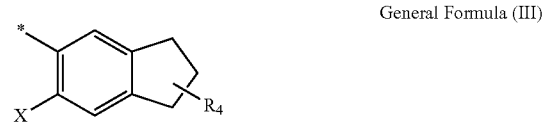

General Formula (III)

where, in General Formulas (II) and (III),
X represents a hydrogen atom or a halogen atom,
$R_4$ represents a methyl group, a dimethyl group or an oxygen atom, and
* represents a binding position.

20 Claims, 13 Drawing Sheets

COMPOUND, KINESIN SPINDLE PROTEIN INHIBITOR, AND APPLICATION THEREOF

CROSS-REFERENCE TO RELATED APPLICATION

This application is a continuation application of International Application PCT/JP2010/071656 filed on Dec. 3, 2010 and designated the U.S., the entire contents of which are incorporated herein by reference.

FIELD

The embodiments discussed herein are related to: a compound; a kinesin spindle protein inhibitor containing the compound; a pharmaceutical composition containing the kinesin spindle protein inhibitor; a method for inhibiting a kinesin spindle protein using the kinesin spindle protein inhibitor; and a preventing or treating method using the pharmaceutical composition.

BACKGROUND

Kinesin is a motor protein which slides over microtubules using adenosine triphosphate and transports, for example, organelles and vesicles, playing an important role in a diverse variety of cell biological processes such as cell division and intracellular substance transportation (e.g., nerve axonal transportation).

At present, about 100 kinds of kinesin-like proteins have been identified. These proteins are presumed to play a very important role during mitosis of the cell cycle by directly interacting with microtubules or chromosomes of the mitotic spindle.

Cell division is a phenomenon that is indispensable for organisms to live and maintain homeostasis of internal environment. Meanwhile, it is also important that apoptosis occurs in organisms to maintain homeostasis. That is, cell division (proliferation) and apoptosis occurring in a balanced manner maintain homeostasis of internal environment of organisms.

However, when such a balance between cell division and apoptosis is lost to enhance cell division, cell proliferative diseases such as cancer develop.

In view of this, attempts have been made to inhibit the kinesin as a treating method for cell proliferative diseases such as cancer. Chemotherapeutic agents routinely used for treating cancer are, for example, taxanes and vinca alkaloids. Taxanes and vinca alkaloids act on microtubules existing in various kinds of cell structures. Presumably, these drugs break the mitotic spindle to inhibit division of cancer cells and induce death of the cancer cells.

Microtubules, however, have an important role not only in cancer cells but also normal cells such as nerve cells. Therefore, these routinely-used chemotherapeutic agents do not specifically target the mitotic spindle, causing problematic side effects of nerve disorders such as numbness in limbs.

A kinesin spindle protein (also called KSP, Eg5, KNSL1, TRIP5 or KIF11, for example), which is one of the identified kinesin-like proteins, is known to localize at the mitotic spindle and be responsible for formation and functions of the bipolar mitotic spindle (see Anne Blangy et al., "Phosphorylation by p34cdc2 regulates spindle association of human Eg5, a kinesin-related motor essential for bipolar spindle formation in vivo" Cell, Vol. 83, pp. 1159-1169, 1995).

Eg5 is known to involve the development of neurons of mice but disappears from neurons immediately after birth, suggesting that the inhibition of Eg5 does not cause peripheral nerve disorders accompanied by routinely-used chemotherapeutic agents (see Lotfi Ferhat et al., "Expression of the mitotic motor protein Eg5 in postmitotic neurons: implications for neuronal development" Journal of Neuroscience 18(19), pp. 7822-7835, 1998).

Therefore, at present, demand has arisen for the provision of a low-molecular-weight new compound capable of inhibiting a kinesin spindle protein with high efficiency; a kinesin spindle protein inhibitor containing the low-molecular-weight compound; and a pharmaceutical composition containing the kinesin spindle protein inhibitor, capable of preventing or treating disorders mediated at least partially by a kinesin spindle protein, free of adverse side effects, and having high safety.

SUMMARY

According to an aspect of the embodiments, a compound is represented by the following General Formula (I):

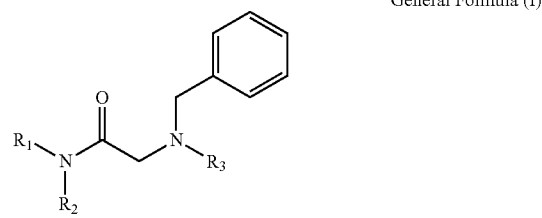

General Formula (I)

where, in General Formula (I), $R_1$ and $R_2$ each represent an alkyl group which may have a substituent, $R_3$ represents the following General Formula (II) or (III), and $R_1$ and $R_2$ may be identical or different,

General Formula (II)

General Formula (III)

where, in General Formulas (II) and (III),

X represents a hydrogen atom or a halogen atom, $R_4$ represents a methyl group, a dimethyl group or an oxygen atom, and

* represents a binding position.

The object and advantages of the invention will be realized and attained by means of the elements and combinations particularly pointed out in the claims. It is to be understood that both the foregoing general description and the following detailed description are exemplary and explanatory and are not restrictive of the invention.

DESCRIPTION OF EMBODIMENTS (New Compound)

The disclosed new compound is represented by the following General Formula (I).

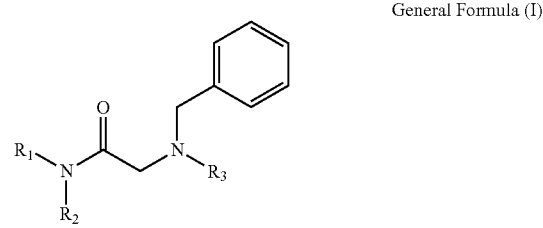

General Formula (I)

In General Formula (I), $R_1$ and $R_2$ each represent an alkyl group which may have a substituent, $R_3$ represents the following General Formula (II) or (III), and $R_1$ and $R_2$ may be identical or different.

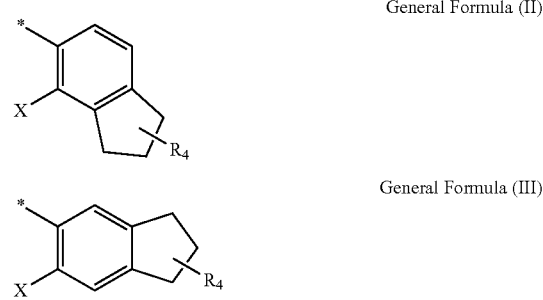

General Formula (II)

General Formula (III)

In General Formulas (II) and (III), X represents a hydrogen atom or a halogen atom, $R_4$ represents a methyl group, a dimethyl group or an oxygen atom, and * represents a binding position.

The compound represented by General Formula (1) may be a pharmacologically acceptable salt or ester, or may be a tautomer.

The salt thereof is not particularly limited and may be appropriately selected depending on the intended purpose. Examples thereof include carboxylates, inorganic acid salts, amino acid salts and sulfonates.

Examples of the carboxylates include trifluoroacetates, acetates, trichloroacetates, hydroxyacetates, lactates, citrates, tartarates, oxalates, benzoates, butyrates, maleates, propionates, formates and malates.

Examples of the inorganic acid salts include hydrohalic acid salts, sulfates, nitrates, phosphates and carbonates.

Examples of the amino acid salts include alginates, aspartates and glutamates.

Examples of the sulfonates include methanesulfonates and p-toluenesulfonates.

Among them, the compound represented by General Formula (I) is preferably a compound represented by the following General Formula (IV), (V) or (VI).

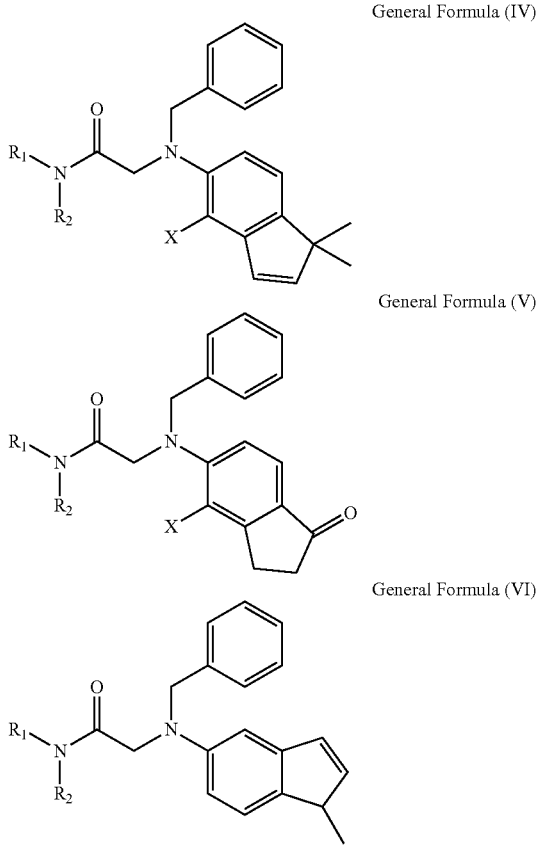

General Formula (IV)

General Formula (V)

General Formula (VI)

In General Formulas (IV), (V) and (VI), $R_1$ and $R_2$ each represent an alkyl group which may have a substituent, X represents a hydrogen atom or a halogen atom, and $R_1$ and $R_2$ may be identical or different.

In General Formulas (I) to (VI), $R_1$ or $R_2$ is or both $R_1$ and $R_2$ are preferably an ethyl group or a methyl group, and $R_1$ and $R_2$ are more preferably the same group.

Also, in General Formulas (I) to (VI), X is preferably a hydrogen atom, a fluorine atom or a chlorine atom.

<Compound Represented by General Formula (IV)>

The compound represented by General Formula (IV) is not particularly limited and may be appropriately selected depending on the intended purpose, but is preferably a compound represented by the following Structural Formula (1).

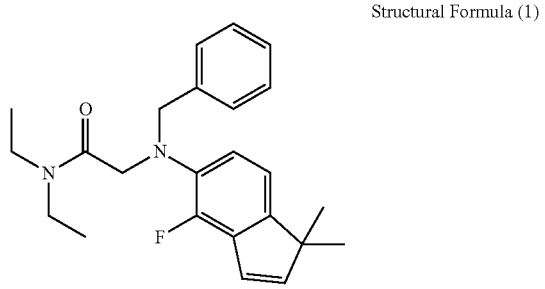

Structural Formula (1)

—Physicochemical Properties—

Physicochemical properties of the compound represented by Structural Formula (1) are as follows.

(1) Molecular formula: $C_{24}H_{29}FN_2O$, molecular weight: 380.23

Figure 1:
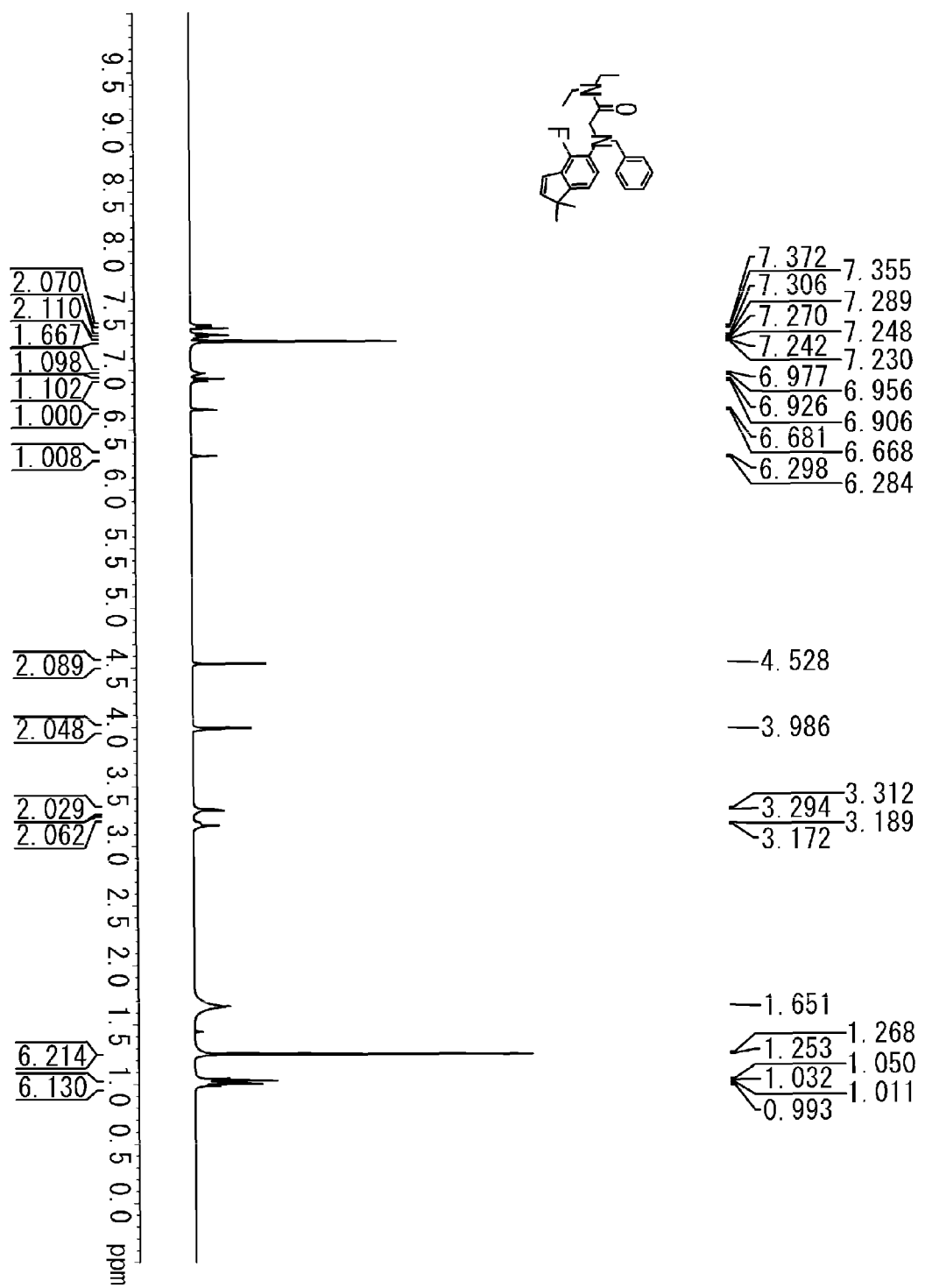
FIG. 1 is a proton nuclear magnetic resonance spectrum of a compound represented by Structural Formula (1), which is one preferred example of a compound represented by General Formula (I)

(2) Proton nuclear magnetic resonance (NMR) was performed in deuterated chloroform ($CDCl_3$) at 400 MHz and 25° C. Its proton nuclear magnetic resonance spectrum is presented in FIG. 1.

Figure 2A:
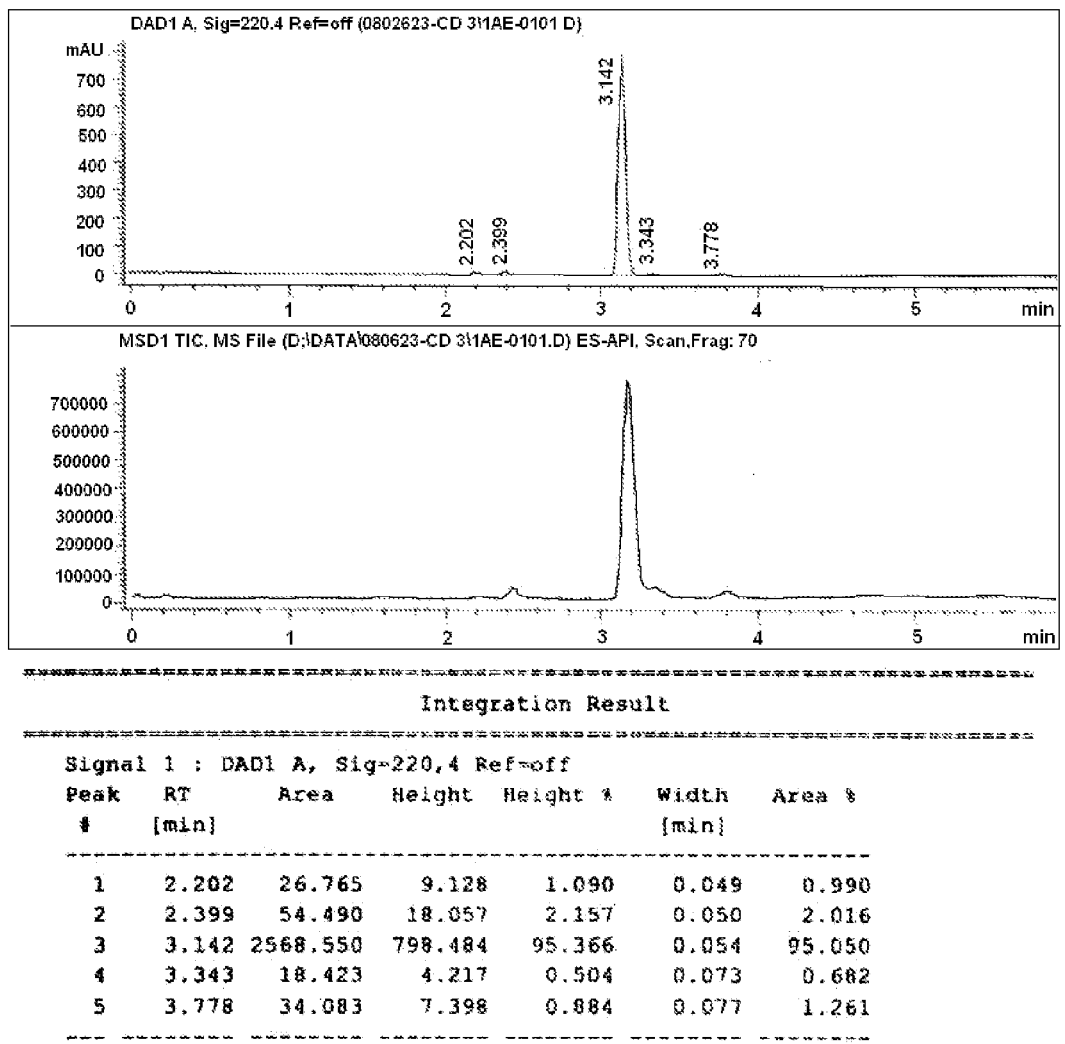
FIG. 2A depicts a chromatograph image of LC (liquid chromatography) (upper graph) and a chromatograph image of MS (mass spectrometry) (lower graph) obtained through high-performance liquid chromatograph-mass spectrometry of a compound represented by Structural Formula (1), which is one preferred example of a compound represented by General Formula (I)
Figure 2B:
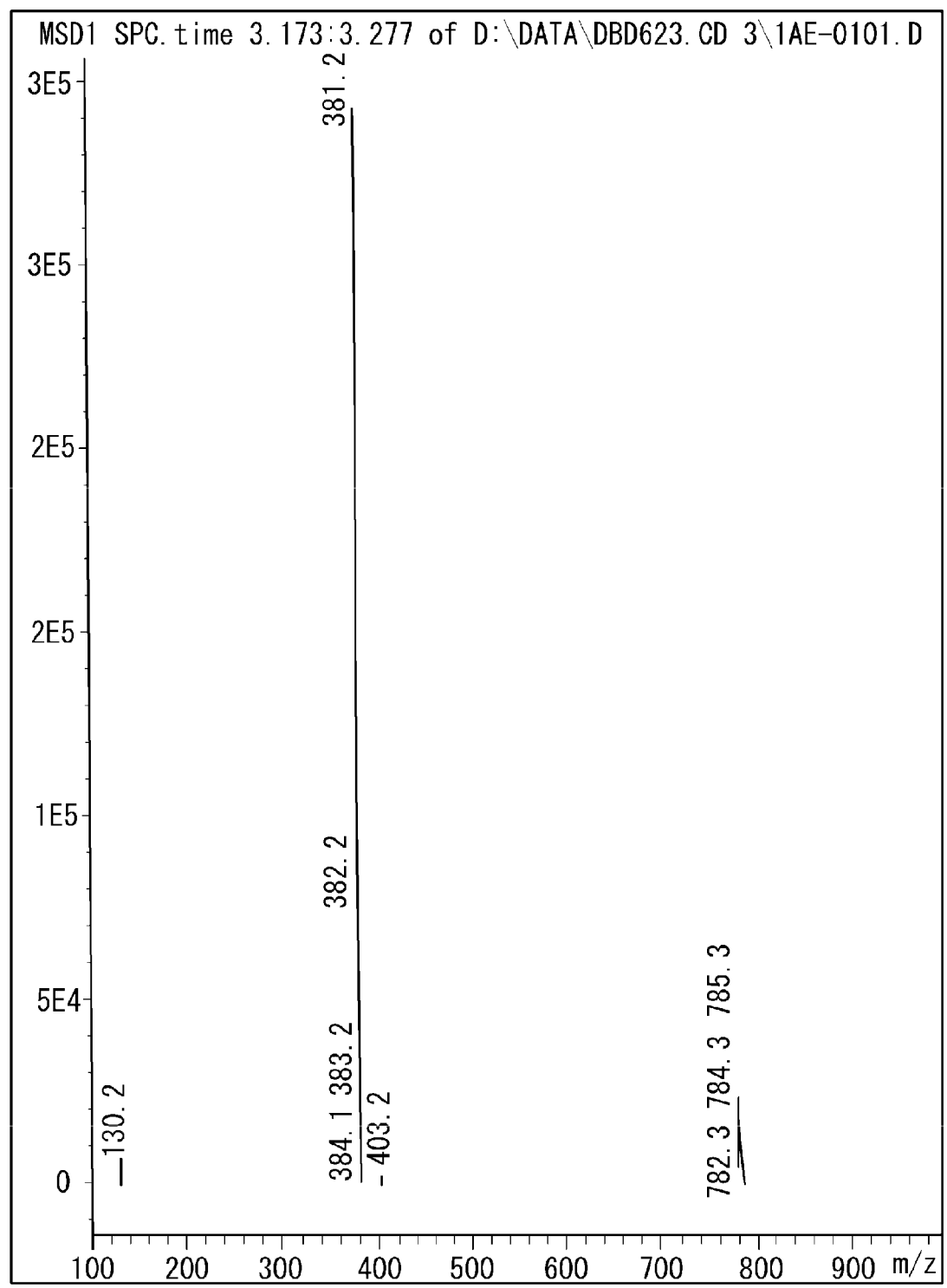
FIG. 2B depicts results of mass spectrometry of an ingredient corresponding to a peak at a retention time of 3.142 in high-performance liquid chromatograph-mass spectrometry of a compound represented by Structural Formula (1), which is one preferred example of a compound represented by General Formula (I)

(3) As a result of measurement with a high-performance liquid chromatograph-mass spectrometer (LC-MS: positive ion mode), the experimental value is m/z 381.2 (M+H)+, and the calculated value of M is m/z 381.23 ($C_{24}H_{30}FN_2O$). The analysis results are presented in FIG. 2A. In FIG. 2A, the upper graph is a chromatograph image of LC (liquid chromatography) (vertical axis: signal intensity (mAU); horizontal axis: measurement time (min)), and the lower graph is a chromatograph image of MS (mass spectrometry) (vertical axis: signal intensity (mAU); horizontal axis: measurement time (min)). Also, FIG. 2B presents results of mass spectrometry of the ingredient corresponding to the peak at a retention time of 3.142.

<<Production Method>>

A production method for the compound represented by General Formula (IV) is not particularly limited and may be appropriately selected depending on the intended purpose, but is, for example, a method through chemical synthesis.

Taking the compound represented by Structural Formula (1) as an example, next will be described one exemplary production method for the compound represented by General Formula (IV).

The method for producing the compound represented by Structural Formula (1) through chemical synthesis is not particularly limited and may be appropriately selected depending on the intended purpose. Examples thereof include a method in which 2-fluorobenzoic acid (compound 1) given in the following scheme is used as a starting compound to synthesize the compound represented by Structural Formula (1) via intermediates.

The method for producing the compound represented by Structural Formula (1) from the starting compound 2-fluorobenzoic acid is, for example, a method in which the compound represented by Structural Formula (1) is produced via 10 intermediates.

Examples of the intermediates include the following compound 2 in the first place (hereinafter may be referred to as "Intermediate 1-1"), the following compound 3 in the second place (hereinafter may be referred to as "Intermediate 1-2"), the following compound 4 in the third place (hereinafter may be referred to as "Intermediate 1-3"), the following compound 5 in the fourth place (hereinafter may be referred to as "Intermediate 1-4"), the following compound 6 in the fifth place (hereinafter may be referred to as "Intermediate 1-5"), the following compound 7 in the sixth place (hereinafter may be referred to as "Intermediate 1-6"), the following compound 8 in the seventh place (hereinafter may be referred to as "Intermediate 1-7"), the following compound 9 in the eighth place (hereinafter may be referred to as "Intermediate 1-8"), the following compound 10 in the ninth place (hereinafter may be referred to as "Intermediate 1-9") and the following compound 11 in the tenth place (hereinafter may be referred to as "Intermediate 1-10").

A method for producing the Intermediates 1-1 to 1-10 is not particularly limited and may be appropriately selected depending on the intended purpose. Examples thereof include a method through chemical synthesis. Alternatively, a commercially available product may be used without chemical synthesis.

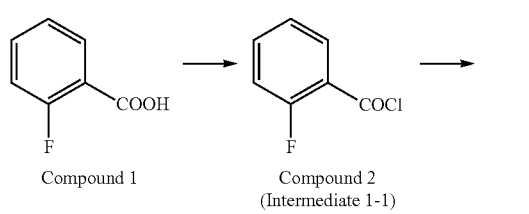

Compound 1 → Compound 2 (Intermediate 1-1)

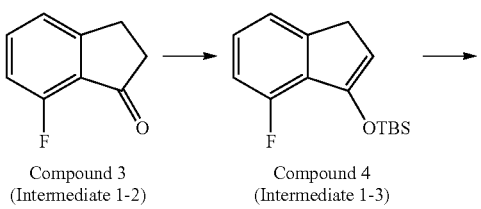

Compound 3 (Intermediate 1-2) → Compound 4 (Intermediate 1-3)

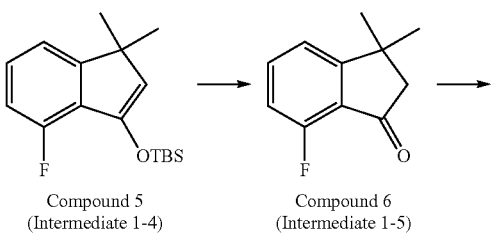

Compound 5 (Intermediate 1-4) → Compound 6 (Intermediate 1-5)

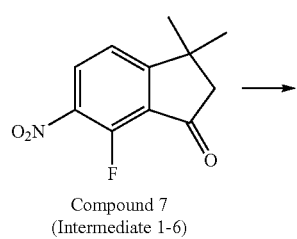

Compound 7 (Intermediate 1-6)

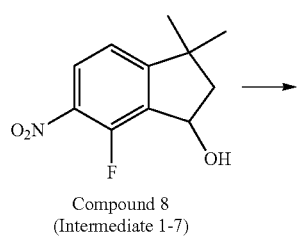

Compound 8 (Intermediate 1-7)

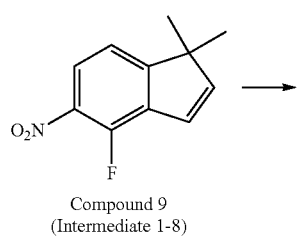

Compound 9 (Intermediate 1-8)

-continued

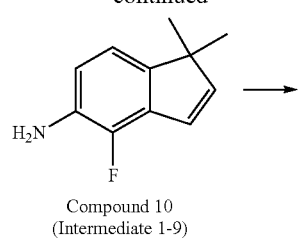

Compound 10 (Intermediate 1-9)

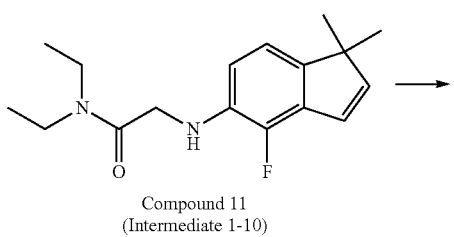

Compound 11 (Intermediate 1-10)

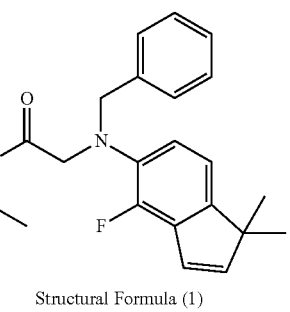

Structural Formula (1)

The reaction temperature, reaction time, synthesis method and amounts of compounds used when the compound represented by General Formula (IV) and the above Intermediates 1-1 to 1-10 are chemically synthesized are not particularly limited and may be appropriately selected depending on the intended purpose.

The state of each compound used in the above chemical synthesis is not particularly limited and may be appropriately selected depending on the intended purpose. It is, for example, in a liquid state, a solid state, a dried state, an oily state or a recrystallized state.

A method for confirming the intermediates is not particularly limited and may be appropriately selected depending on the intended purpose. Examples thereof include an analysis method using, for example, proton nuclear magnetic resonance spectrometry, mass spectrometry, 13C nuclear magnetic resonance spectrometry, infrared spectrometry or high-performance liquid chromatography.

The product obtained by the above chemical synthesis may be purified, if necessary.

A method for the purification is not particularly limited and may be appropriately selected depending on the intended purpose. Examples thereof include a method using a column containing normal-phase or reverse-phase filler, prep-TLC (preparative TLC) and prep-HPLC (preparative HPLC).

<Compound Represented by General Formula (V)>

The compound represented by General Formula (V) is not particularly limited and may be appropriately selected depending on the intended purpose, but is preferably a compound represented by the following Structural Formula (2).

Structural Formula (2)

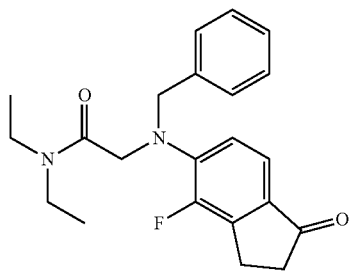

—Physicochemical Properties—

Figure 9:
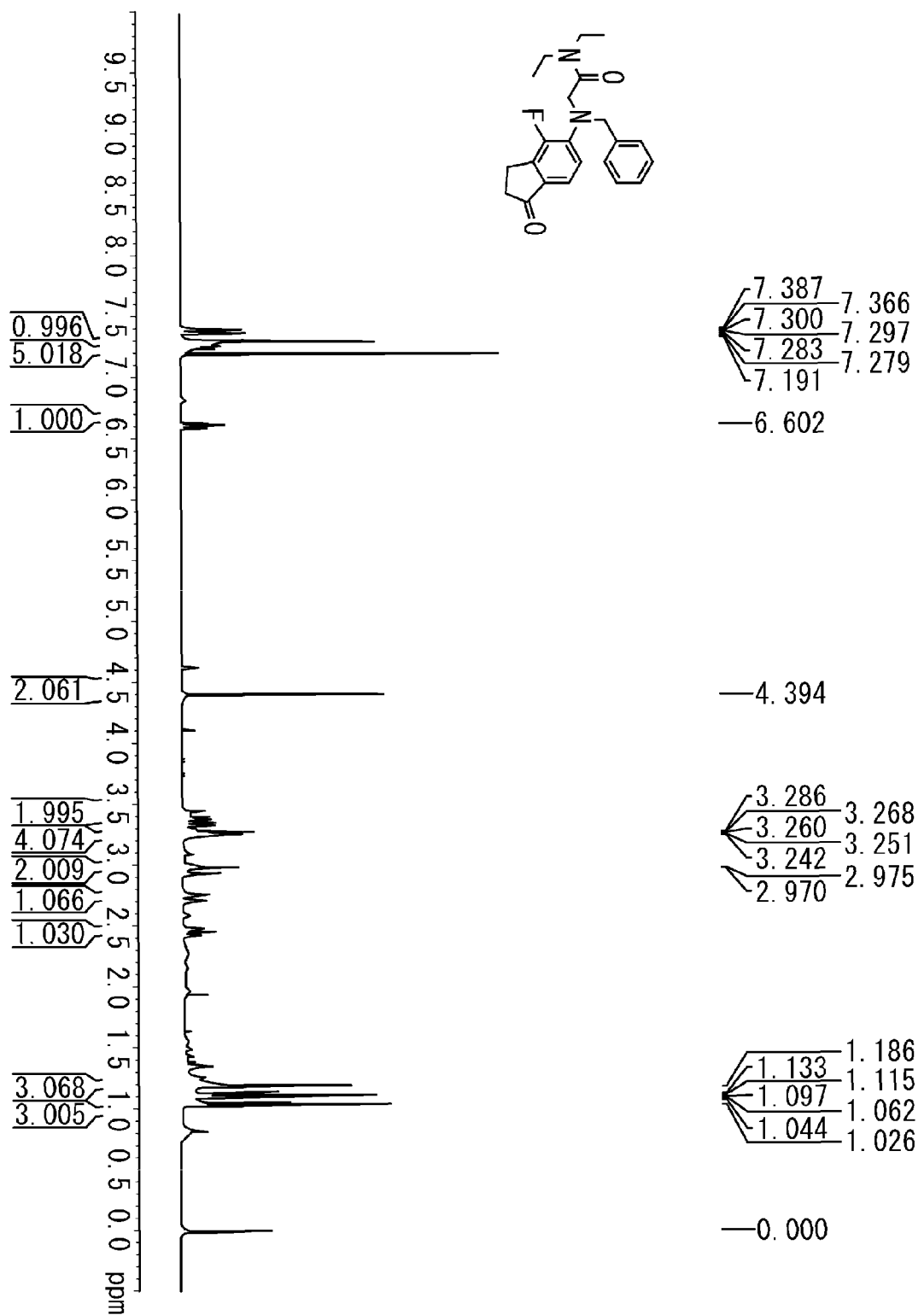
FIG. 9 is a proton nuclear magnetic resonance spectrum of a compound represented by Structural Formula (2), which is one preferred example of a compound represented by General Formula (V)

Physicochemical properties of the compound represented by Structural Formula (2) are as follows.
(1) Molecular formula: $C_{22}H_{25}FN_2O_2$, molecular weight: 368.44
(2) Proton nuclear magnetic resonance (NMR) was performed in deuterated chloroform ($CDCl_3$) at 400 MHz and 25° C. Its proton nuclear magnetic resonance spectrum is presented in FIG. 9.

<<Production Method>>

A production method for the compound represented by General Formula (V) is not particularly limited and may be appropriately selected depending on the intended purpose, but is, for example, a method through chemical synthesis.

Taking the compound represented by Structural Formula (2) as an example, next will be described one exemplary production method for the compound represented by General Formula (V).

The method for producing the compound represented by Structural Formula (2) through chemical synthesis is not particularly limited and may be appropriately selected depending on the intended purpose. Examples thereof include a method in which 4-chloro-2-fluoroaniline is used as a starting compound to produce the compound represented by Structural Formula (2) via intermediates.

The method for producing the compound represented by Structural as Formula (2) from 4-chloro-2-fluoroaniline is not particularly limited and may be appropriately selected depending on the intended purpose. It is, for example, a method in which the compound represented by Structural Formula (2) is produced via 8 intermediates as presented below.

Examples of the intermediates include
N-(4-chloro-2-fluorophenyl)acetamide in the first place (hereinafter may be referred to as "Intermediate 2-1"),
N-(4-chloro-2-fluoro-3-formylphenyl)acetamide in the second place (hereinafter may be referred to as "Intermediate 2-2"),
(E)-ethyl-3-(3-acetamide-6-chloro-2-fluorophenyl)acrylate in the third place (hereinafter may be referred to as "Intermediate 2-3"),
(E)-3-(3-acetamide-6-chloro-2-fluorophenyl)acrylic acid in the fourth place (hereinafter may be referred to as "Intermediate 2-4"),
3-(3-acetamide-2-fluorophenyl)propanoic acid in the fifth place (hereinafter may be referred to as "Intermediate 2-5"),
N-(4-fluoro-1-oxo-2,3-dihydro-1H-inden-5-yl)acetamide in the sixth place (hereinafter may be referred to as "Intermediate 2-6"),
5-amino-4-fluoro-2,3-dihydro-1H-inden-1-one in the seventh place (hereinafter may be referred to as "Intermediate 2-7") and
5-(benzylamino)-4-fluoro-2,3-dihydro-1H-inden-1-one in the eighth place (hereinafter may be referred to as "Intermediate 2-8").

A method for producing the Intermediates 2-1 to 2-8 is not particularly limited and may be appropriately selected depending on the intended purpose. Examples thereof include a method through chemical synthesis. Alternatively, a commercially available product may be used.

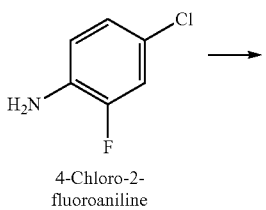

4-Chloro-2-fluoroaniline

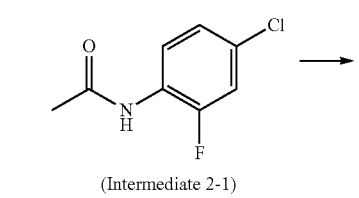

(Intermediate 2-1)

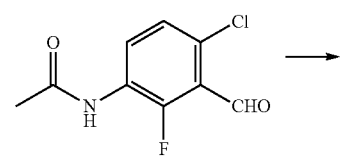

(Intermediate 2-2)

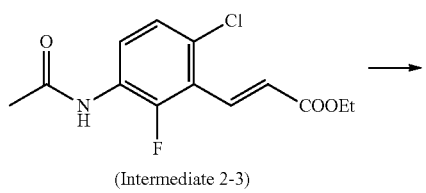

(Intermediate 2-3)

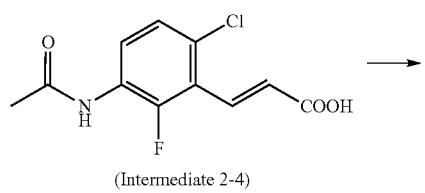

(Intermediate 2-4)

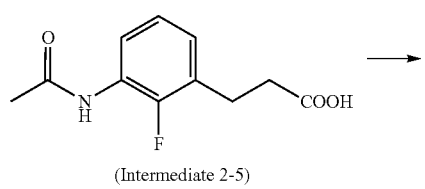

(Intermediate 2-5)

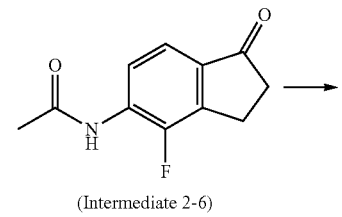

(Intermediate 2-6)

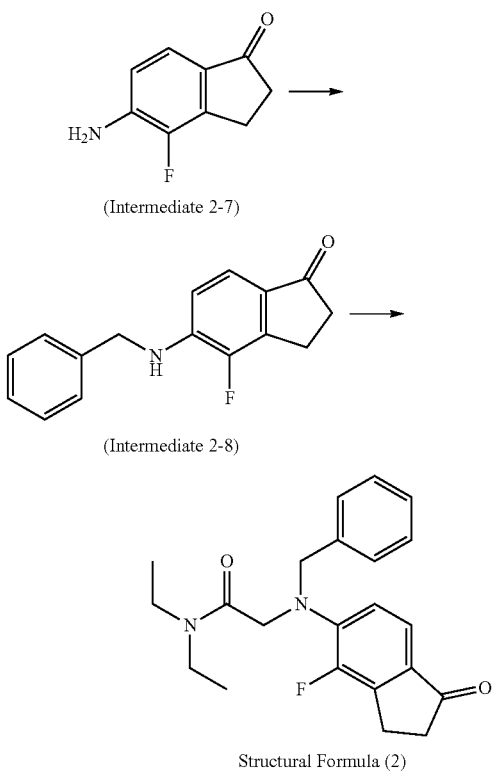

(Intermediate 2-7)

(Intermediate 2-8)

Structural Formula (2)

The reaction temperature, reaction time, synthesis method and amounts of compounds used when the compound represented by General Formula (V) and the above Intermediates 2-1 to 2-8 are chemically synthesized are not particularly limited and may be appropriately selected depending on the intended purpose.

The state of each compound used in the above chemical synthesis is not particularly limited and may be appropriately selected depending on the intended purpose. It is, for example, in a liquid state, a solid state, a dried state, an oily state or a recrystallized state.

A method for confirming the intermediates is not particularly limited and may be appropriately selected depending on the intended purpose. Examples thereof include an analysis method using, for example, proton nuclear magnetic resonance spectrometry, mass spectrometry, 13C nuclear magnetic resonance spectrometry, infrared spectrometry or high-performance liquid chromatography.

The product obtained by the above chemical synthesis may be purified, if necessary.

A method for the purification is not particularly limited and may be appropriately selected depending on the intended purpose. Examples thereof include a method using a column containing normal-phase or reverse-phase filler, prep-TLC and prep-HPLC.

<Compound Represented by General Formula (VI)>

The compound represented by General Formula (VI) is not particularly limited and may be appropriately selected depending on the intended purpose, but is preferably a compound represented by the following Structural Formula (3) or (4).

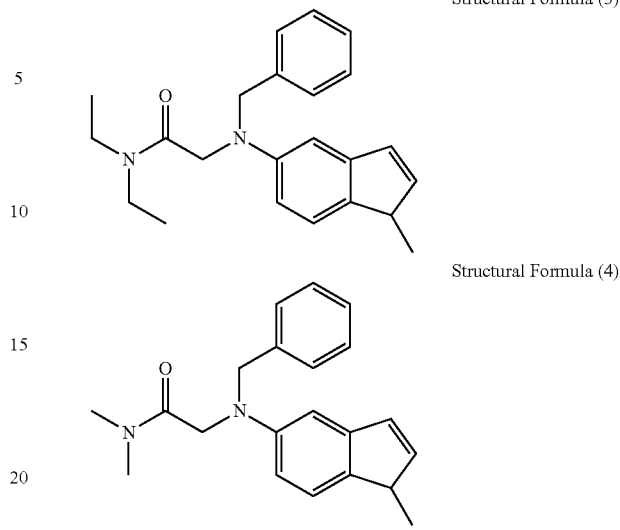

—Physicochemical Properties—

Figure 11:
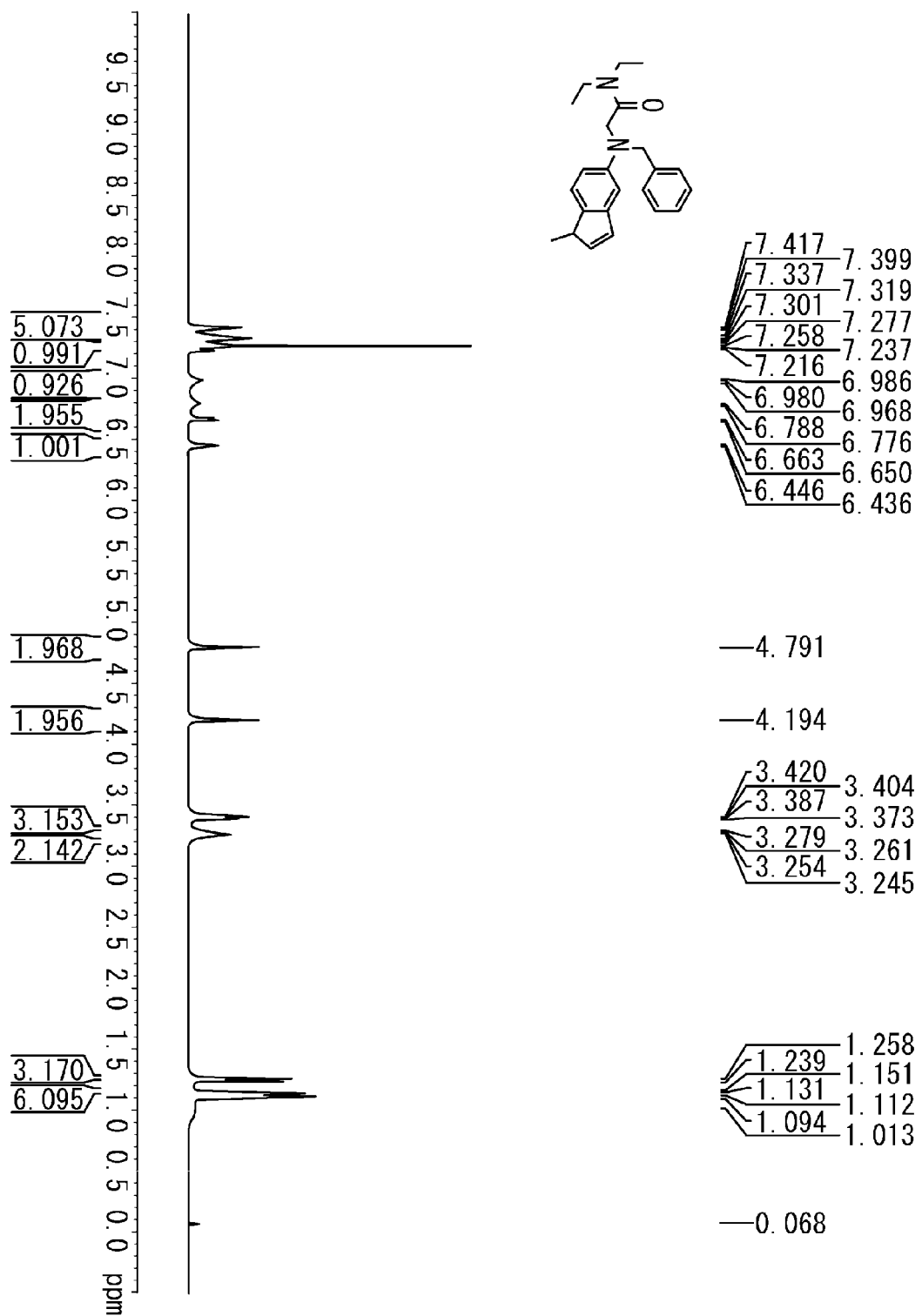
FIG. 11 is a proton nuclear magnetic resonance spectrum of a compound represented by Structural Formula (3), which is one preferred example of a compound represented by General Formula (VI)

Physicochemical properties of the compound represented by Structural Formula (3) are as follows.
(1) Molecular formula: $C_{23}H_{28}N_2O$, molecular weight: 348.48
(2) Proton nuclear magnetic resonance (NMR) was performed in deuterated chloroform ($CDCl_3$) at 400 MHz and 25° C. Its proton nuclear magnetic resonance spectrum is presented in FIG. 11.

Figure 12:
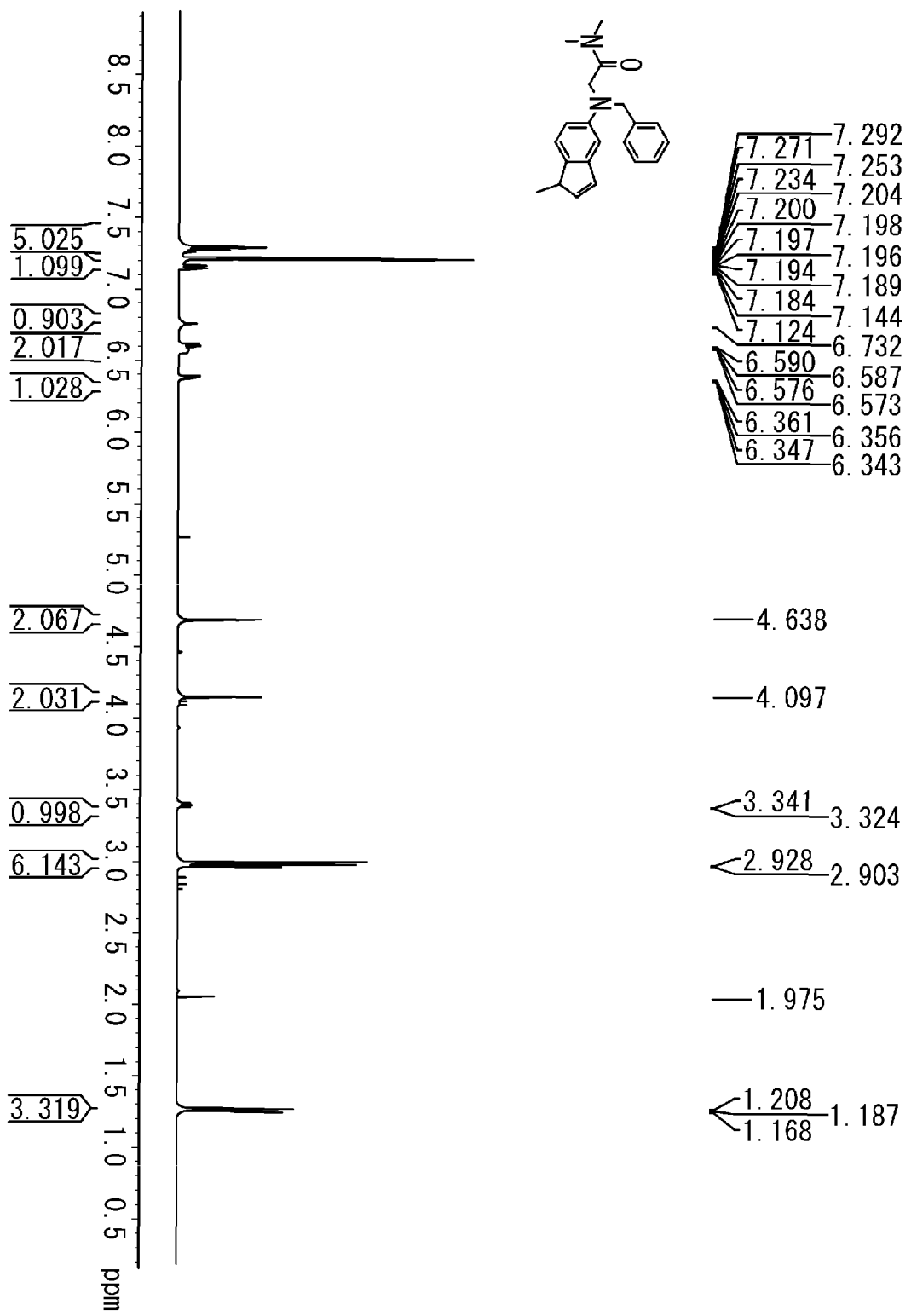
FIG. 12 is a proton nuclear magnetic resonance spectrum of a compound represented by Structural Formula (4), which is one preferred example of a compound represented by General Formula (VI).

Physicochemical properties of the compound represented by Structural Formula (4) are as follows.
(1) Molecular formula: $C_{21}H_{24}N_2O$, molecular weight: 320.43
(2) Proton nuclear magnetic resonance (NMR) was performed in deuterated chloroform ($CDCl_3$) at 400 MHz and 25° C. Its proton nuclear magnetic resonance spectrum is presented in FIG. 12.

<<Production Method>>

A production method for the compound represented by General Formula (VI) is not particularly limited and may be appropriately selected depending on the intended purpose, but is, for example, a method through chemical synthesis.

Taking the compound represented by Structural Formula (3) or (4) as an example, next will be described one exemplary production method for the compound represented by General Formula (VI).

The method for producing the compound represented by Structural Formula (3) or (4) through chemical synthesis is not particularly limited and may be appropriately selected depending on the intended purpose. Examples thereof include a method in which bromobenzene given below is used as a starting compound to produce the compound represented by Structural Formula (3) or (4) via intermediates.

The method for producing the compound represented by Structural Formula (3) or (4) from the starting compound bromobenzene is not particularly limited and may be appropriately selected depending on the intended purpose. It is, for example, a method in which the compound represented by Structural Formula (3) or (4) is produced via 10 intermediates as presented below.

Examples of the intermediates include phenyllithium in the first place (hereinafter may be referred to as "Intermediate 3-1"), 3-phenylbutanoic acid in the second place (hereinafter may be referred to as "Intermediate 3-2"), 3-methyl-2,3-dihydro-1H-inden-1-one in the third place (hereinafter may be referred to as "Intermediate 3-3"), 3-methyl-6-nitro-2,3-dihydro-1-H-inden-1-one in the fourth place (hereinafter may be referred to as "Intermediate 3-4"), 6-amino-3-methyl-2,3-dihydro-1-H-inden-1-one in the fifth place (hereinafter may be referred to as "Intermediate 3-5"), N-(1-methyl-3-oxo-indan-5-yl)benzamide in the sixth place (hereinafter may be referred to as "Intermediate 3-6"), [benzyl-(1-methyl-3-oxo-indan-6-yl)-amino]-acetic acid ethyl ester in the seventh place (hereinafter may be referred to as "Intermediate 3-7"), [benzyl-(3-hydroxy-1-methyl-indan-5-yl)-amino]-acetic acid ethyl ester in the eighth place (hereinafter may be referred to as "Intermediate 3-8"), [benzyl-(3-hydroxy-1-H-indan-5-yl)-amino]-acetic acid ethyl ester in the ninth place (hereinafter may be referred to as "Intermediate 3-9") and [benzyl-(3-hydroxy-1-H-indan-5-yl)-amino]-acetic acid ethyl ester in the tenth place (hereinafter may be referred to as "Intermediate 3-10").

A method for producing the Intermediates 3-1 to 3-10 is not particularly limited and may be appropriately selected depending on the intended purpose. Examples thereof include a method through chemical synthesis. Alternatively, a commercially available product may be used.

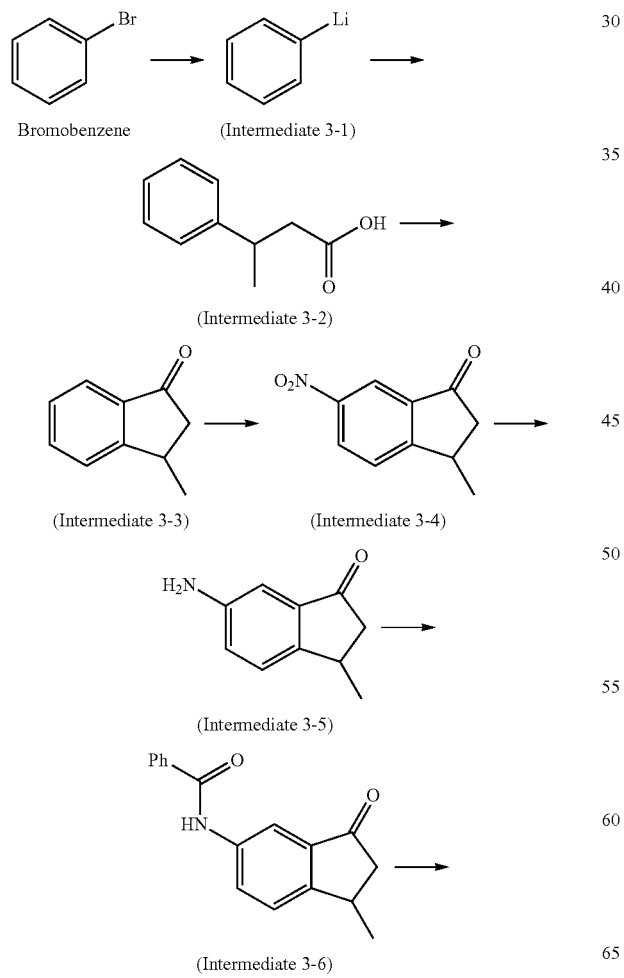

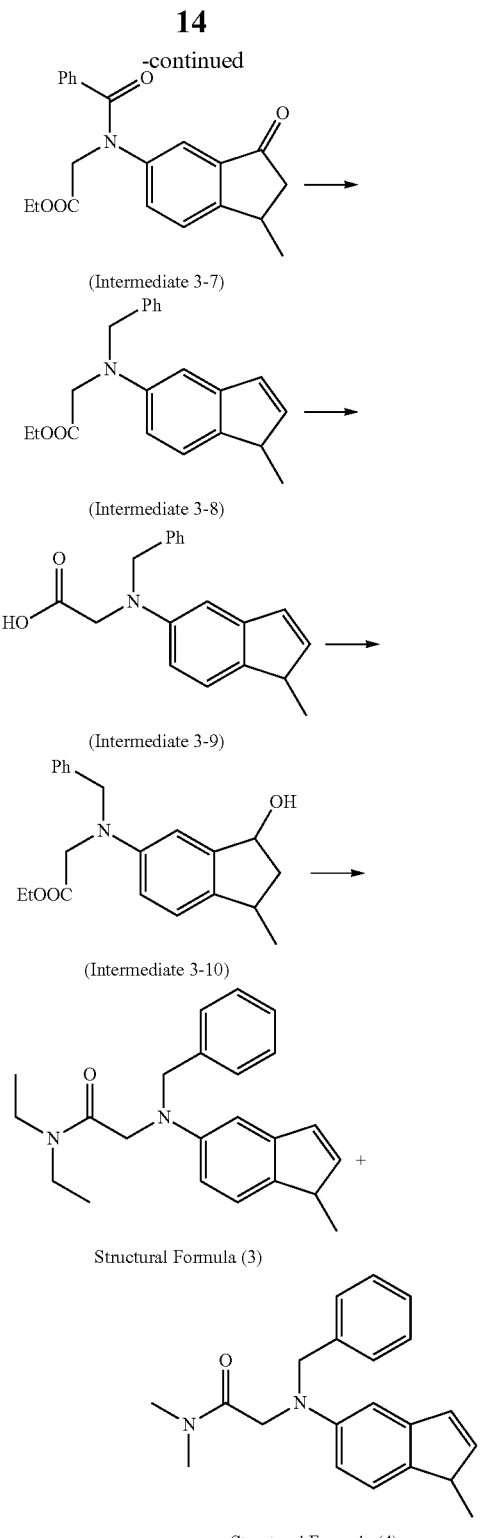

The reaction temperature, reaction time, synthesis method and amounts of compounds used when the compound represented by General Formula (VI) and the above Intermediates 3-1 to 3-10 are chemically synthesized are not particularly limited and may be appropriately selected depending on the intended purpose.

The state of each compound used in the above chemical synthesis is not particularly limited and may be appropriately selected depending on the intended purpose. It is, for example, in a liquid state, a solid state, a dried state, an oily state or a recrystallized state.

A method for confirming the intermediates is not particularly limited and may be appropriately selected depending on the intended purpose. Examples thereof include an analysis method using, for example, proton nuclear magnetic resonance spectrometry, mass spectrometry, 13C nuclear magnetic resonance spectrometry, infrared spectrometry or high-performance liquid chromatography.

The product obtained by the above chemical synthesis may be purified, if necessary.

A method for the purification is not particularly limited and may be appropriately selected depending on the intended purpose. Examples thereof include a method using a column containing normal-phase or reverse-phase filler, prep-TLC (preparative TLC) and prep-HPLC (preparative HPLC).

(Kinesin Spindle Protein Inhibitor)

A kinesin spindle protein inhibitor contains the compound represented by General Formula (I); and, if necessary, further contains other ingredients.

<Compound Represented by General Formula (I)>

The compound represented by General Formula (I) in the kinesin spindle protein inhibitor may be used alone or in combination of two or more thereof.

An amount of the compound represented by General Formula (I) in the kinesin spindle protein inhibitor is not particularly limited and may be appropriately selected depending on the intended purpose so long as the activity of a kinesin spindle protein can be inhibited. The kinesin spindle protein inhibitor may be the compound represented by General Formula (I) itself.

<Other Ingredients>

The other ingredients are not particularly limited and may be appropriately selected from pharmacologically acceptable carriers depending on the intended purpose. Examples thereof include pharmacologically acceptable carriers.

<Dosage Form>

A dosage form of the kinesin spindle protein inhibitor is not particularly limited, and examples thereof include a solid preparation, a semi-solid preparation and a liquid preparation.

—Solid Preparation—

The solid preparation is not particularly limited and may be appropriately selected depending on the intended purpose. When it is used as an internal preparation, examples of the solid preparation include tablets, chewable tablets, foaming tablets, orally-disintegrating tablets, troches, drops, hard capsules, soft capsules, granules, powder, pills, dry syrups and infusions.

When the solid preparation is an external preparation, examples of the solid preparation include suppositories, cataplasms and plasters.

—Semi-Solid Preparation—

The semi-solid preparation is not particularly limited and may be appropriately selected depending on the intended purpose. When it is used as an as internal preparation, examples of the semi-solid preparation include electuaries, chewing gums, whip and jelly.

When the semi-solid preparation is used as an external preparation, examples of the semi-solid preparation include ointments, cream, mousse, inhaler and nasal gel.

—Liquid Preparation—

The liquid preparation is not particularly limited and may be appropriately selected depending on the intended purpose. When it is used as an internal preparation, examples of the liquid preparation include syrups, drinks, suspensions and spirits.

When the liquid preparation is used as an external preparation, examples of the liquid preparation include liquid, eye drops, aerosol and sprays.

(Method for Inhibiting Kinesin Spindle Protein)

The activity of a kinesin spindle protein can be inhibited by bringing the kinesin spindle protein inhibitor and cells into contact with each other.

<Kinesin Spindle Protein Inhibitor>

An amount of the kinesin spindle protein inhibitor used is not particularly limited and may be appropriately selected depending on the intended purpose so long as the activity of the kinesin spindle protein in the cells can be inhibited.

The kinesin spindle protein inhibitor may be used alone or in combination with another kinesin spindle protein inhibitor.

<Cells>

The cells are not particularly limited and may be appropriately selected depending on the intended purpose. Examples thereof include cells in vivo and cultured cells.

—Cells In Vivo—

A method for bringing the kinesin spindle protein inhibitor and the cells in vivo into contact with each other is not particularly limited and may be appropriately selected depending on the intended purpose. Examples thereof include a method in which the kinesin spindle protein inhibitor is administered to a subject to be administered such as animals.

The animal species serving as the subject to be administered is not particularly limited and may be appropriately selected depending on the intended purpose. Examples of the animal species include human, monkey, pig, bovine, sheep, goat, dog, cat, mouse, rat and bird.

A method for the administration is not particularly limited and may be appropriately selected depending on the site where the inhibition of the activity of the kinesin spindle protein is intended. Examples thereof include a local administration method, an enteral administration method and a parenteral administration method.

The local administration method is not particularly limited and may be appropriately selected depending on the intended purpose. Examples thereof include an epicutaneous administration method, an inhalation administration method, an infusion administration method, a method of administering eye drops on the conjunctiva, an intranasal administration method and an intravaginal administration method.

The enteral administration method is not particularly limited and may be appropriately selected depending on the intended purpose. Examples thereof include a peroral administration method, a tube feeding method and an enema administration method.

The parenteral administration method is not particularly limited and may be appropriately selected depending on the intended purpose. Examples thereof include an intravenous administration method, an intra-arterial administration method, an intramuscular administration method, an intracardiac administration method, a subcutaneous administration method, an intraosseous administration method, an intracutaneous administration method, an intrathecal administration method, an intraperitoneal administration method, an intravesical administration method, a percutaneous administration method, a mucosal administration method, an inhalation administration method, an epidural administration method and an intravitreal administration method.

The dose of the kinesin spindle protein inhibitor administered is not particularly limited and may be appropriately selected considering various factors of a subject to be administered, such as the age, body weight, constitution, symptom and the presence or absence of administration of a drug containing other active ingredients.

—Cultured Cells—

The cultured cells are not particularly limited and may be appropriately selected depending on the intended purpose.

The cultured cells may be a known cultured cell line, primary cultured cells taken from animals, or subcultured cells of the primary cultured cells.

The number of the cultured cells is not particularly limited and may be appropriately selected depending on the intended purpose.

A method for bringing the kinesin spindle protein inhibitor and the cultured cells into contact with each other is not particularly limited and may be appropriately selected depending on the intended purpose. Examples thereof include a method in which the kinesin spindle protein inhibitor is added to a medium where the cultured cells are cultured.

The amount of the kinesin spindle protein inhibitor added is not particularly limited and may be appropriately selected depending on, for example, the number of the cultured cells.

(Pharmaceutical Composition and Preventing or Treating Method)

A pharmaceutical composition contains the kinesin spindle protein inhibitor and, if necessary, further contains other ingredients.

Use of the pharmaceutical composition can prevent or treat disorders mediated at least partially by a kinesin spindle protein.

<Pharmaceutical Composition>
<<Kinesin Spindle Protein Inhibitor>>

The amount of the kinesin spindle protein inhibitor in the pharmaceutical composition is not particularly limited and may be appropriately selected depending on the intended purpose so long as the disorders can be prevented or treated. The kinesin spindle protein inhibitor may be contained alone or in combination of two or more thereof. Also, the pharmaceutical composition may be the kinesin spindle protein inhibitor itself.

<<Other Ingredients>>

The other ingredients are not particularly limited and may be appropriately selected depending on the intended purpose so long as the effects of the present invention are not impeded. Examples thereof include pharmacologically acceptable carriers and drugs containing other active ingredients.

The amount of the other ingredients in the pharmaceutical composition is not particularly limited and may be appropriately selected depending on the intended purpose.

—Pharmacologically Acceptable Carrier—

The pharmacologically acceptable carrier is not particularly limited and may be appropriately selected depending on the intended purpose. Examples thereof include a freshener, a disinfectant, a preserving agent, a binding agent, a thickener, an adhesive agent, an integrating agent, a colorant, a stabilizer, a pH adjuster, a buffer, a tonicity agent, a solvent, an antioxidant, a UV rays-preventing agent, a preventing agent for precipitation of crystals, a defoaming agent, a property improving agent and an antiseptic agent.

The binding agent, thickener and adhesive agent are not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyol cellulose, hydroxypropyolmethyl cellulose, carboxymethyl starch, pullulan, sodium alginate, ammonium alginate, propylene glycol alginic acid esters, guar gum, locust bean gum, gum Arabic, xanthane gum, gelatin, casein, polyvinyl alcohol, polyethylene oxide, polyethylene glycol, ethylene/propylene block polymers, sodium polyacrylates and polyvinylpyrrolidone. These may be used alone or in combination of two or more thereof.

The integrating agent is not particularly limited and may be appropriately selected depending on the intended purpose. Examples of the integrating agent include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone.

The colorant is not particularly limited and may be appropriately selected depending on the intended purpose. Examples thereof include titanium oxide and iron oxide.

The stabilizer is not particularly limited and may be appropriately selected depending on the intended purpose. Examples thereof include tragacanth, gum Arabic, gelatin, sodium pyrosulfite, EDTA, thioglycolic acid and thiolactic acid.

The pH adjuster and the buffer are not particularly limited and may be appropriately selected depending on the intended purpose. Examples thereof include sodium citrate, sodium acetate and sodium phosphate.

The tonicity agent is not particularly limited and may be appropriately selected depending on the intended purpose. Examples thereof include sodium chloride and glucose.

—Drugs Containing Other Active Ingredients—

The drugs containing other active ingredients are not particularly limited and may be appropriately selected depending on the intended purpose, but are preferably drugs used for treating or preventing cancer.

The drugs used for treating or preventing cancer are not particularly limited and may be appropriately selected depending on the intended purpose. Examples thereof include drugs containing active ingredients such as BCG (bacille Calmette-Guerin), actinomycin D, aclarubicin, azacytidine, asparaginase, aceglatone, anastrozole, aminoglutethimide, amsacrine, alemtuzumab, allopurinol, anthracycline, androgen, bicalutamide, anti-androgen, ibritumomab, ifosfamide, imatinib, irinotecan, interferon, interferon-α, interleukin-2, ubenimex, exemestane, estramustine, estrogen, etoposide, enocitabine, epirubicin, oxaliplatin, octreotide, carboquone, carboplatin, carmustine, carmofur, cladribine, clarithromycin, krestin (PSK), chlorambucil, ketoconazole, gefitinib, gemcitabine, gemtuzumab, goserelin, thalidomide, cyclophosphamide, cisplatin, schizophyllan, cytarabine, cyproheptadine, zinostatin stimalamer, streptozocin, suramin, sobuzoxane, tamoxifen, targretin, daunorubicin, dacarbazine, dactinomycin, thioguanine, thiotepa, tegafur, tegafur.uracil, tegafur.gimeracil.oteracil potassium, teniposide, dexamethasone, denileukin diftitox, topotecan, trastuzumab, triptorelin, tretinoin, toremifene, doxifluridine, doxorubicin, docetaxel, nimustine, neocarzinostatin, nedaplatin, valrubicin, paclitaxel, hydroxyurea, hydroxycarbamide, bicalutamide, vinorelbine, vincristine, vindesine, vinblastine, picibanil, pirarubicin, fadrozole, fluorouracil, flutamide, fludarabine, fulvestrant, floxuridine, busulfan, bleomycin, plicamycin, prednisone, procarbazine, procarbazine, peplomycin, pemetrexed, pentostatin, porfimer sodium, mitomycin, mitoxantrone, mitotane, mechlorethamine, mesna, methysergide, methotrexate, medroxyprogesterone, melacine, mercaptopurine, melphalan, ranimustine, rituximab, leuprolide, letrozole, levamisole, lentinan, leucovorin, lomustine, arsenic trioxide, megestrol acetate, radioactive iodine-131 and radioactive phosphorus. These may be used alone or in combination of two or more thereof.

<<Use>>

The pharmaceutical composition may be used alone or in combination of two or more thereof. Also, the pharmaceutical composition may be used in combination with a drug containing other active ingredients, or may be formulated into a drug containing other active ingredients before use.

<<Disorders Mediated by Kinesin Spindle Protein>>

The disorders are not particularly limited and may be appropriately selected depending on the intended purpose, but are preferably cell proliferative diseases, more preferably cancerous diseases.

The cancerous diseases are not particularly limited and may be appropriately selected depending on the intended purpose. Examples thereof include lung cancer, bronchial cancer, prostate cancer, breast cancer, pancreas cancer, colon cancer, rectal cancer, small intestinal cancer, thyroid cancer, esophageal cancer, oral cancer, pharyngeal cancer, larynx cancer, stomach cancer, liver cancer, intrahepatic bile duct cancer, kidney cancer, renal pelvis cancer, bladder cancer, uterine corpus cancer, uterocervical cancer, ovary cancer, conjunctival cancer, lacrimal cancer, palpebral cancer, multiple myeloma, brain tumor, non-Hodgkin's lymphoma, melanoma, trophoblastic colon adenoma, acute myelocytic leukemia, chronic myelocytic leukemia, lymphatic leukemia and myelocytic leukemia.

<Preventing or Treating Method>

A preventing or treating method for the disorders mediated at least partially by a knesin spindle protein is not particularly limited and may be appropriately selected depending on the intended purpose so long as the pharmaceutical composition is used.

Examples thereof include a method in which the pharmaceutical composition is administered to a subject to be administered before or after development of the disorders.

The dose, subject and timing for the administration are not particularly limited and may be appropriately selected depending on the intended purpose.

Examples of the animal species serving as the subject to be administered include human, monkey, pig, bovine, sheep, goat, dog, cat, mouse, rat and bird.

A method for the administration is not particularly limited and may be appropriately selected depending on the intended purpose. Examples thereof include methods similar to those for administration of the kinesin spindle protein inhibitor.

The dose of the pharmaceutical composition administered is not particularly limited and may be appropriately selected considering various factors of a subject to be administered, such as the age, body weight, constitution, symptom and the presence or absence of administration of a drug containing other active ingredients.

Hereinafter, the examples of the present invention will be specifically explained, but these examples shall not be construed as to limit the scope of the present invention.

PRODUCTION EXAMPLE 1

Synthesis of Compound Represented by Structural Formula (1)

<Synthesis of Compound 2>

As presented in the following reaction formula, a mixture of 2-fluorobenzoic acid (10 g, 71 mmol) and thionyl chloride ($SOCl_2$; 9 mL) was allowed to react at 40° C. for 30 min, followed by removing of the solvent. The obtained compound was used for the next step without purification.

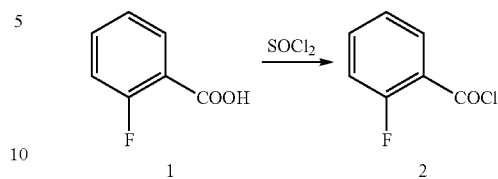

<Synthesis of Compound 3>

As presented in the following reaction formula, a crude product of Compound 2 was dissolved in methylene chloride (50 mL). Under cooling with ice, aluminum chloride ($AlCl_3$; 13 g, 9.7 mmol) and sodium chloride (NaCl; 6 g, 10 mmol) were added to the resulting solution, and ethylene gas was introduced for 2 hours to the mixture under stirring. Then, 100 g of ice was added to the reaction mixture, followed by filtrating. The filtrate was extracted three times with 30 mL of ether and then washed with 100 mL of saturated brine. The filtrate was dried and concentrated with anhydrous sodium sulfate, and purified with a silica gel column of 100 g using n-hexane and ethyl acetate, to thereby give Compound 3 of interest (2.5 g, yield: 23%).

<Synthesis of Compound 4>

As presented in the following reaction formula, tert-butyldimethylchlorosilane (TBSCl) (21 g, 140 mmol) was added under cooling with ice to a mixture of Compound 3 (19 g, 127 mmol) and triethylamine ($Et_3N$; 14 g, 138 mmol) in acetonitrile ($CH_3CN$; 100 mL). Next, the mixture was stirred for 1 hour under reflux. The reaction mixture was concentrated to give the residue, which was dissolved in ether (150 mL). The obtained filtrate was dried and concentrated with anhydrous sodium sulfate, to thereby give a crude product of Compound 4. The crude product was used for the next step without purification.

<Synthesis of Compound 5>

As presented in the following reaction formula, the crude product of Compound 4 (32 g) was dissolved in acetonitrile (250 mL). Then, methyl iodide (MeI; 44 g, 310 mmol) and a 29% solution (200 mL) of lithium hexamethyldisilazide (LiHMDS; g, 310 mmol) in tetrahydrofuran were added to the resulting solution, followed by refluxing for 2 hours. Ice water (200 mL) was added to the reaction mixture and extracted three times with 100 mL of ethyl acetate. The combined organic phase was dried and concentrated with anhydrous sodium sulfate, to thereby give a crude product of Compound 5. The crude product was used for the next step without purification.

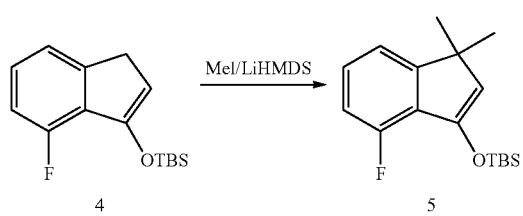 [SMILES: CC(C)(C)[Si](C)(C)OC1=CCc2cccc(F)c21 ; CC1(C)C=C(O[Si](C)(C)C(C)(C)C)c2c(F)cccc21]

<Synthesis of Compound 6>

As presented in the following reaction formula, cesium fluoride (10 g, 66 mmol) was added to a mixture of the crude product of Compound 5 (20.4 g, 77 mmol) in tetrahydrofuran (250 mL), and the mixture was stirred at room temperature for 3 hours. The volume of the tetrahydrofuran was reduced to 100 mL under reduced pressure. Then, 100 mL of ethyl acetate and 100 mL of ice water were added to the mixture, followed by extracting three times with 100 mL of acetic acid. The combined organic phase was washed with 100 mL of saturated brine, and dried and concentrated with anhydrous sodium sulfate, to thereby give Compound 6 (12 g, yield: 53%).

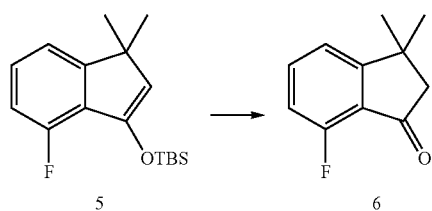 [SMILES: CC1(C)C=C(O[Si](C)(C)C(C)(C)C)c2c(F)cccc21 ; CC1(C)CC(=O)c2c(F)cccc21]

<Synthesis of Compound 7>

As presented in the following reaction formula, a mixture of potassium nitrate ($KNO_3$; 8 g, 81 mmol) and sulfuric acid (20 mL) was added to Compound 6 (12 g, 67 mmol), and the mixture was stirred under cooling with ice for 1 hour and further stirred at room temperature for 2 hours. Then, 200 mL of ice water was added to the mixture, followed by extracting three times with 100 mL of acetic acid. The combined organic phase was washed with saturated brine, and dried and concentrated with anhydrous sodium sulfate, to thereby give Compound 7a (5 g, yield: 33%) and Compound 7b (4 g, yield: 27%).

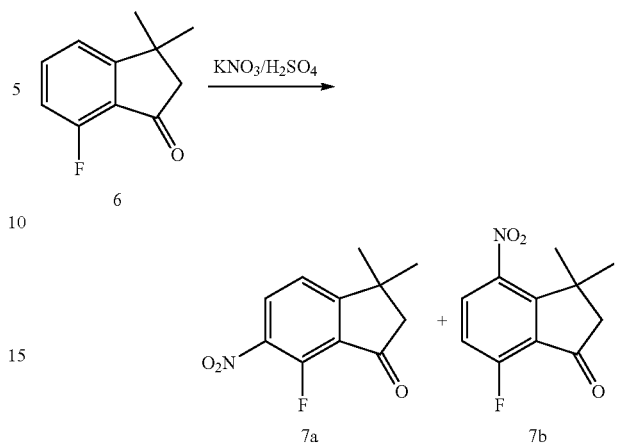

<Synthesis of Compound 8>

As presented in the following reaction formula, a mixture of Compound 7a (5 g, 22 mmol) and sodium borohydride ($NaBH_4$; 1 g, 26 mmol) in ethanol (50 mL) was stirred at room temperature for 1 hour. Then, 100 mL of water was added to the mixture, followed by extracting three times with 100 mL of ethyl acetate. The combined organic phase was washed with 100 mL of saturated brine, and dried and concentrated with anhydrous sodium sulfate, to thereby give a crude product of Compound 8. The crude product was used for the next step without purification.

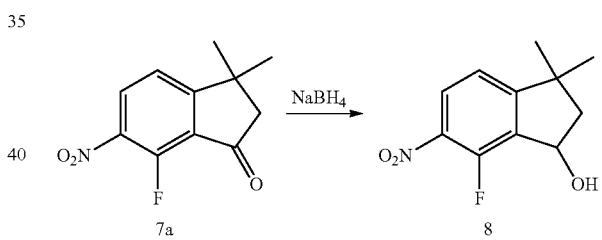

<Synthesis of Compound 9>

As presented in the following reaction formula, Compound 8 (3 g, 13 mmol) and p-trisulfonic acid catalyst (TsOH (cat.); 200 mg) were dissolved in 30 mL of toluene, and the solution was refluxed for 3 hours. After concentration of the toluene of the reaction mixture, 30 mL of water was added thereto, followed by extracting three times with 30 mL of ethyl acetate. The combined organic phase was dried and concentrated with anhydrous sodium sulfate, to thereby give Compound 9 (2.5 g, yield: 90%).

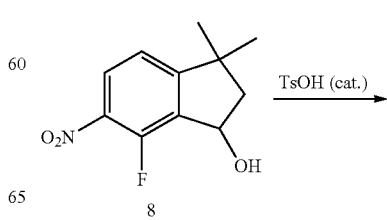

-continued

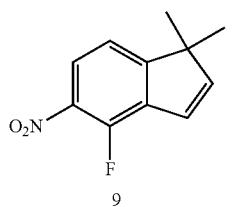

9

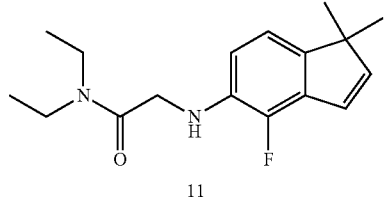

11

<Synthesis of Compound 10>

As presented in the following reaction formula, hydrochloric acid (HCl; 15.5 mL) was added at room temperature to Compound 9 (2.5 g, 12 mmol) and tin chloride ($SnCl_2$; 5.7 g, 30 mmol), and the mixture was stirred at 60° C. for 2 hours. Then, 50 mL of ice water was added to the reaction mixture, followed by extracting three times with 30 mL of ethyl acetate. The combined organic phase was dried and concentrated with anhydrous sodium sulfate, to thereby give Compound 10 (1.5 g, yield: 71%).

<Synthesis of Compound Represented by Structural Formula (1)>

As presented in the following reaction formula, triethylamine (50 mg, 0.5 mM) and benzyl bromide (80 mg, 0.5 mM) were added to a mixture of Compound 11 (140 mg, 0.48 mmol) in dimethylformamide (5 mL), and the mixture was heated at 60° C. for 2 hours. Then, 20 mL of water was added to the reaction mixture, followed by extracting three times with 5 mL of ethyl acetate. After evaporation of the solvent, the reaction mixture was purified with prep-HPLC (product of Waters Co., Ltd.), to thereby give a product (15 mg, yield: 8.2%).

Structural Formula (1)

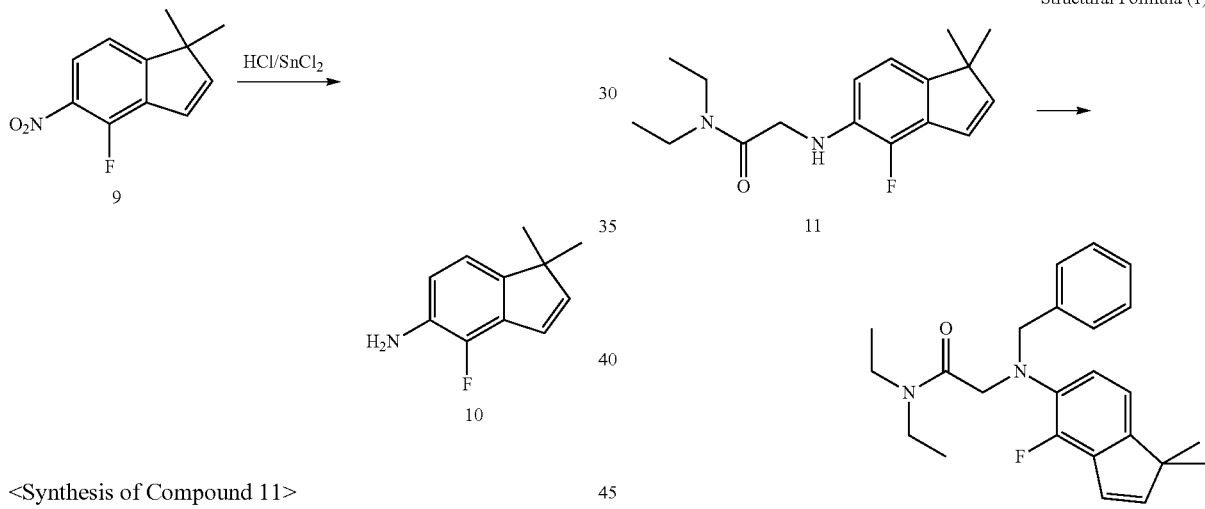

<Synthesis of Compound 11>

As presented in the following reaction formula, triethylamine (300 mg, 30 mM) and iodine acetic acid diethylamide (640 mg, 30 mmol) were added to a mixture of Compound 10 (500 mg, 2.8 mmol) in dimethylformamide (7 mL), and the mixture was stirred at 40° C. for 2 hours. Then, 20 mL of ice water was added to the reaction mixture, followed by extracting three times with 30 mL of ethyl acetate. The combined organic phase was dried and concentrated with anhydrous sodium sulfate, to thereby give Compound 11 (140 mg, yield: 17%).

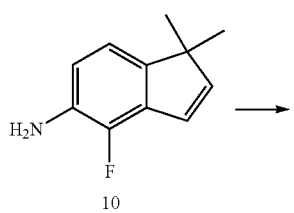

The compound represented by Structural Formula (1) was analyzed through proton nuclear magnetic resonance (NMR) in deuterated chloroform ($CDCl_3$) at 400 MHz and 25° C. The obtained proton nuclear magnetic resonance spectrum is presented in FIG. 1.

In addition, as a result of measurement of the compound represented by Structural Formula (1) with a high-performance liquid chromatograph-mass spectrometer (LC-MS: positive ion mode), the experimental value was m/z 381.2 (M+H)+, and the calculated value of M was m/z 381.23 ($C_{24}H_{30}FN_2O$). The analysis results are presented in FIG. 2A. In FIG. 2A, the upper graph is a chromatograph image of LC (liquid chromatography) (vertical axis: signal intensity (mAU); horizontal axis: measurement time (min)), and the lower graph is a chromatograph image of MS (mass spectrometry) (vertical axis: signal intensity; horizontal axis: measurement time (min)). Also, FIG. 2B presents results of mass spectrometry of the ingredient corresponding to the peak at a retention time of 3.142.

PRODUCTION EXAMPLE 2

Synthesis of Compound Represented by Structural Formula (2)

<Preparation of N-(4-chloro-2-fluorophenyl)acetamide>

As presented in the following reaction formula, anhydrous acetic acid (Ac₂O; 1.7 mL) was added several times in a divided manner to a mixture of 4-chloro-2-fluoroaniline (2 g, 13.8 mmol) in acetic acid (2 mL) at room temperature (about 25° C.). The resulting reaction mixture was stirred for 2 hours. After the completion of reaction, the mixture was filtered to obtain a crude product, which was washed with hexane to obtain N-(4-chloro-2-fluorophenyl)acetamide (2.4 g, yield: 94%).

Figure 3:
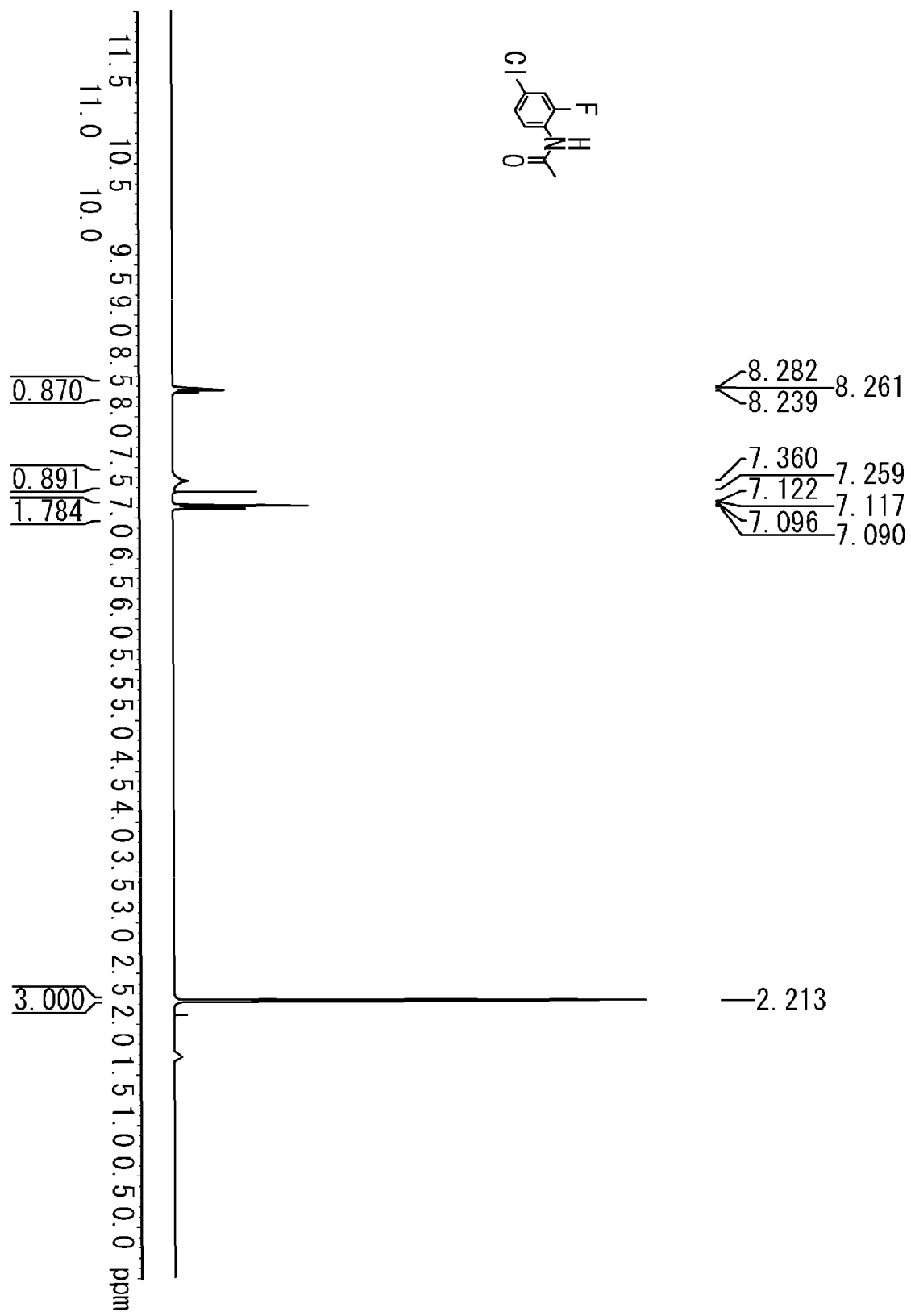
FIG. 3 is a proton nuclear magnetic resonance spectrum of N-(4-chloro-2-fluorophenyl)acetamide; i.e., an intermediate of a compound represented by Structural Formula (2), which is one preferred example of a compound represented by General Formula (V)

The N-(4-chloro-2-fluorophenyl)acetamide was analyzed through proton nuclear magnetic resonance (NMR) in deuterated chloroform (CDCl₃) at 400 MHz and 25° C. The obtained proton nuclear magnetic resonance spectrum is presented in FIG. 3.

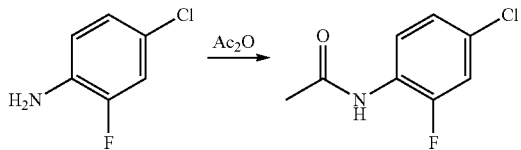

<Preparation of N-(4-chloro-2-fluorophenyl)acetamide>

As presented in the following reaction formula, a solution (166 mL, 0.35 mol) of n-butyllithium (n-BuLi) in hexane was added several times in a divided manner to a solution of N-(4-chloro-2-fluorophenyl)acetamide (30 g, 0.16 mol) in tetrahydrofuran (THF; 300 mL) at −78° C. The resulting reaction mixture was stirred for 1 hour. Then, anhydrous N,N-dimethylformamide (DMF; 10.5 mL, 0.18 mol) was added to the mixture at −78° C. and stirred for another 0.5 hours. The reaction was terminated with saturated ammonium chloride. The organic phase was separated, dried and concentrated to obtain a crude product, which was used for the next step without purification.

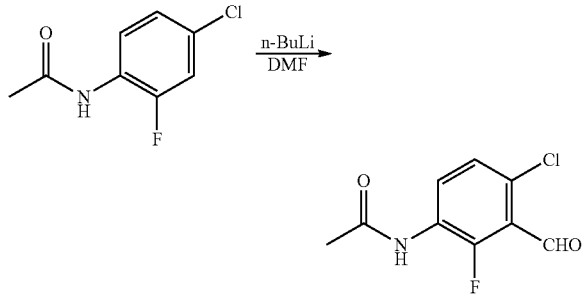

<Preparation of (E)-ethyl 3-(3-acetamido-6-chloro-2-fluorophenyl)acrylate>

Sodium hydroxide (5.3 g, 0.22 mol) was added at 0° C. to a solution of N-(4-chloro-2-fluoro-3-formylphenyl)acetamide and ethyl-2-(diethoxylphosphoryl)acetate (37.6 g, 0.17 mol) in toluene (500 mL). The obtained solution was stirred for 2 hours at room temperature (25° C.). The reaction was terminated with saturated ammonium chloride, and the reaction mixture was extracted three times with 300 mL of ethyl acetate. The organic phase was separated, dried and concentrated to obtain a crude product, which was used for the next step without purification.

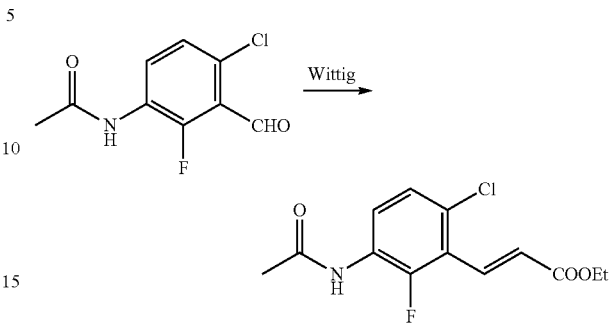

<Preparation of (E)-3-(3-acetamido-6-chloro-2-fluorophenyl)acrylic acid>

An aqueous lithium hydroxide solution (11.3 g, 150 mL, 0.27 mol) was added at room temperature (25° C.) to a mixture of (E)-ethyl-3-(3-acetamido-6-chloro-2-fluorophenyl) acrylate in methanol (150 mL)/tetrahydrofuran (THF; 150 mL). The resulting solution was stirred for 2 hours. The mixture was extracted three times with 30 mL of ethyl acetate. The aqueous phase was adjusted to 1 to 2 in pH with hydrochloride (1 M) and extracted three times with 30 mL of ethyl acetate.

The organic phase was dried and concentrated to obtain a pure product (E)-3-(3-acetamido-6-chloro-2-fluorophenyl) acrylic acid (15 g, yield: 37%). Note that, this yield is a yield after the above three steps.

Figure 4:
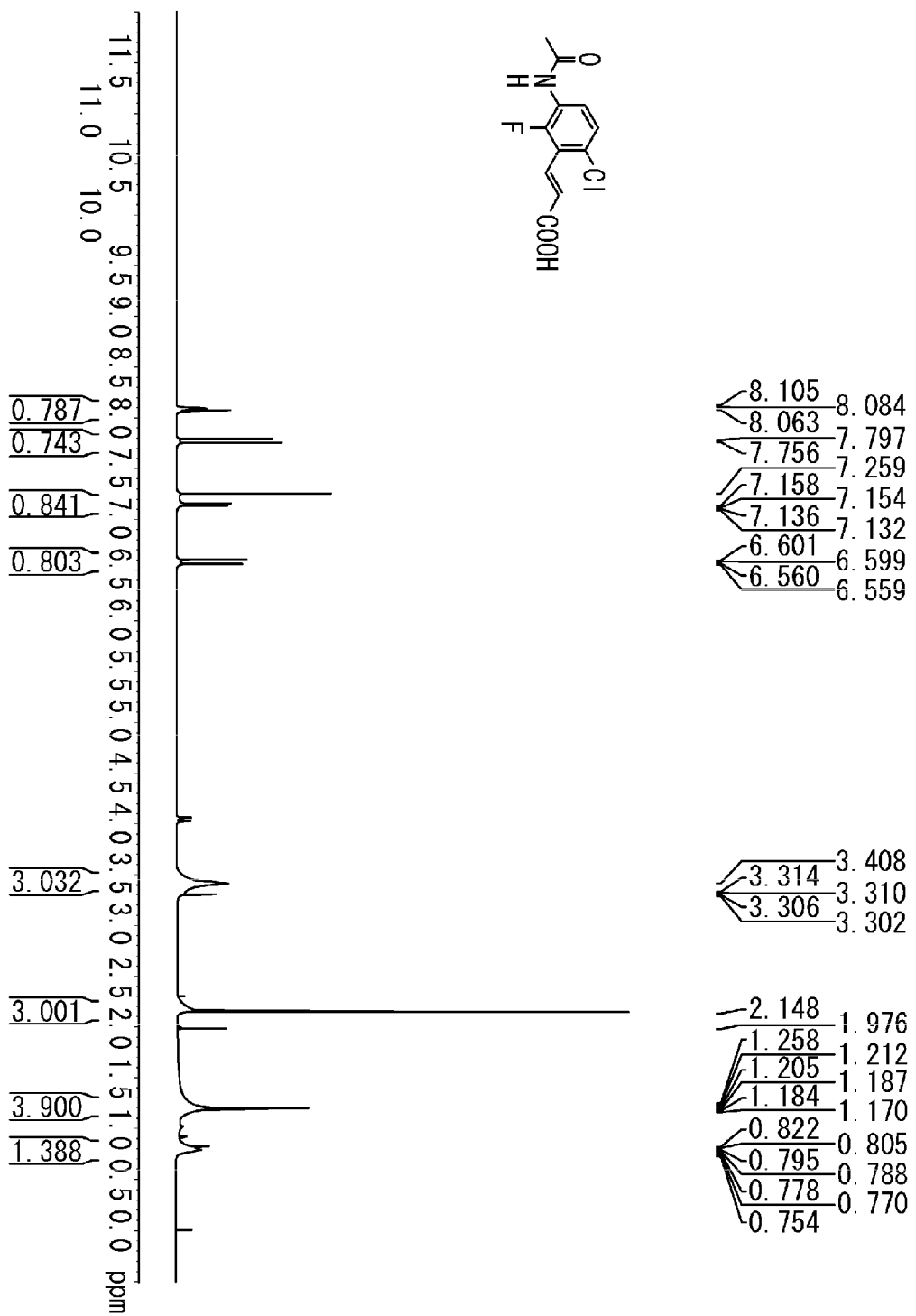
FIG. 4 is a proton nuclear magnetic resonance spectrum of (E)-3-(3-acetamide-6-chloro-2-fluorophenyl)acrylic acid; i.e., an intermediate of a compound represented by Structural Formula (2), which is one preferred example of a compound represented by General Formula (V)

The (E)-3-(3-acetamido-6-chloro-2-fluorophenyl)acrylic acid was analyzed through proton nuclear magnetic resonance (NMR) in deuterated chloroform (CDCl₃) at 400 MHz and 25° C. The obtained proton nuclear magnetic resonance spectrum is presented in FIG. 4.

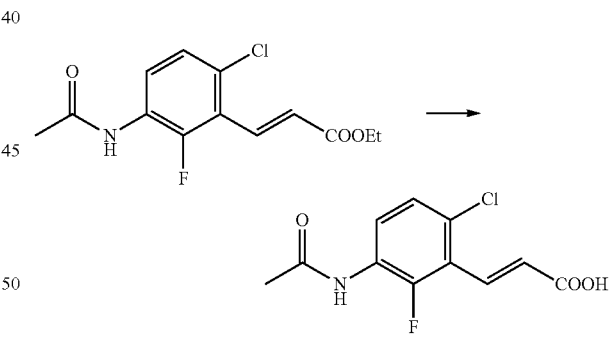

<Preparation of 3-(3-acetamido-2-fluorophenyl)propanoic acid>

As presented in the following reaction formula, a mixture of (E)-3-(3-acetamido-6-chloro-2-fluorophenyl)acrylic acid (15 g, 0.058 mol), palladium carbon (Pd/C; 1.5 g, 5.8 mmol), methanol (100 mL) and triethylamine (6.4 g, 0.06 mol) was stirred under 1 atm (H₂) at 50° C. overnight. The mixture was filtered and concentrated to give 3-(3-acetamido-2-fluorophenyl)propanoic acid (10 g, yield: 73%) as a yellow solid.

Figure 5:
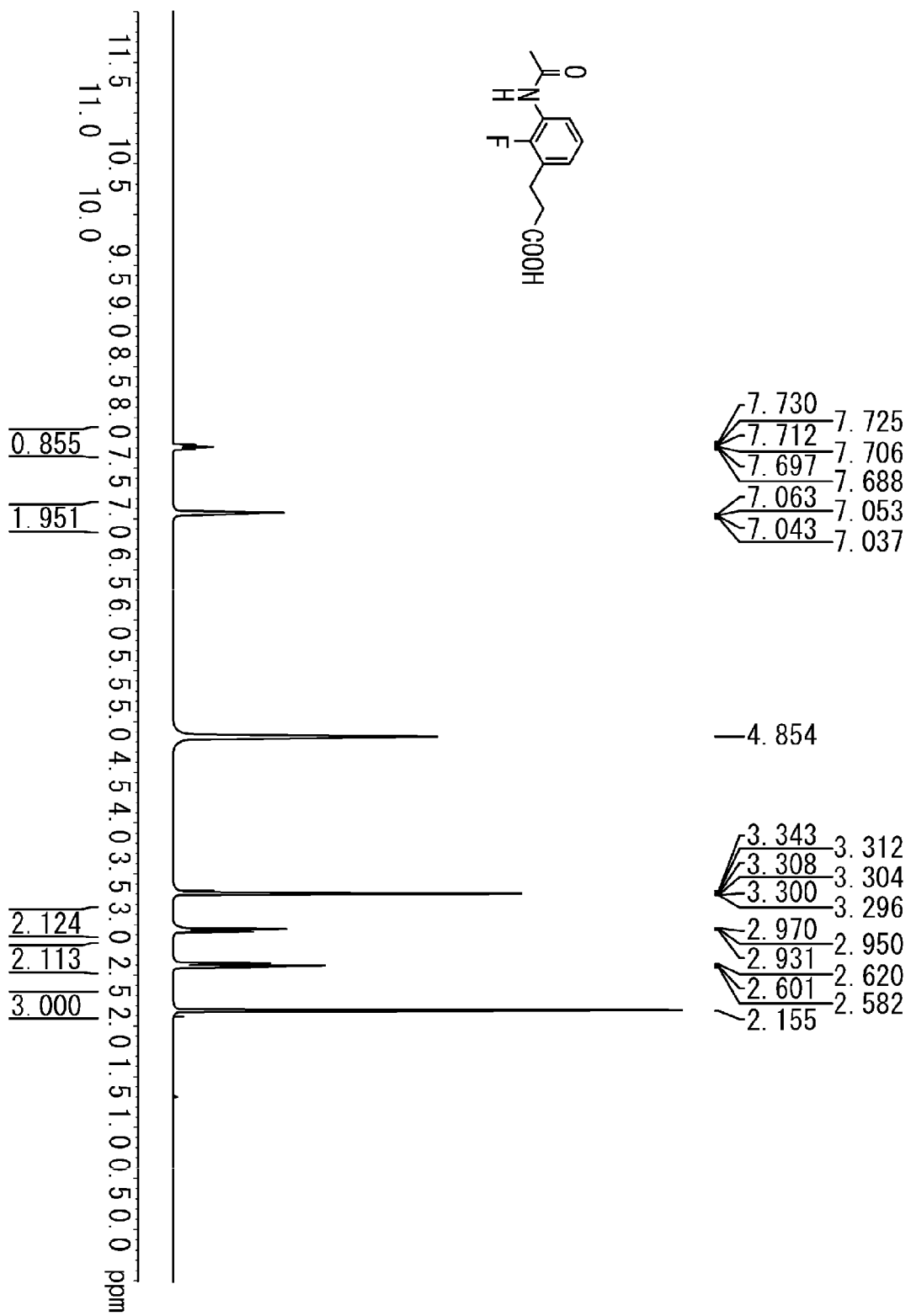
FIG. 5 is a proton nuclear magnetic resonance spectrum of 3-(3-acetamide-2-fluorophenyl)propanoic acid; i.e., an intermediate of a compound represented by Structural Formula (2), which is one preferred example of a compound represented by General Formula (V)

The 3-(3-acetamido-2-fluorophenyl)propanoic acid was analyzed through proton nuclear magnetic resonance (NMR) in deuterated methanol (MeOD) at 400 MHz and 25° C. The obtained proton nuclear magnetic resonance spectrum is presented in FIG. 5.

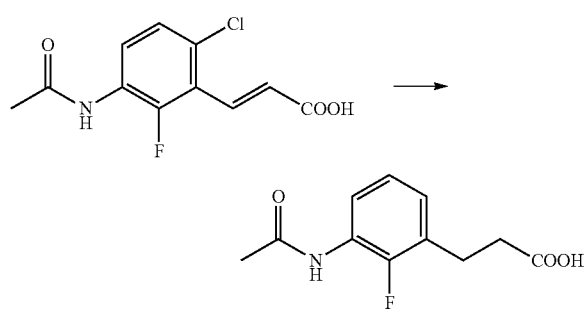

<Preparation of N-(4-fluoro-1-oxo-2,3-dihydro-1H-inden-5-yl)acetamide>

As presented in the following reaction formula, a solution of 3-(3-acetamido-2-fluorophenyl)propanoic acid (10 g, 0.04 mmol) in polyphosphoric acid (20 mL) was stirred at 120° C. for 2 hours. The resulting mixture was treated with 4N sodium hydroxide so that the pH thereof was adjusted to 10 to 12, and then extracted three times with 100 mL of ethyl acetate. The combined organic phase was washed with saturated brine (100 mL), and dried and concentrated with anhydrous sodium sulfate, to thereby give N-(4-fluoro-1-oxo-2,3-dihydro-1H-inden-5-yl)acetamide (3.0 g, yield: 38%) as a yellow solid.

Figure 6:
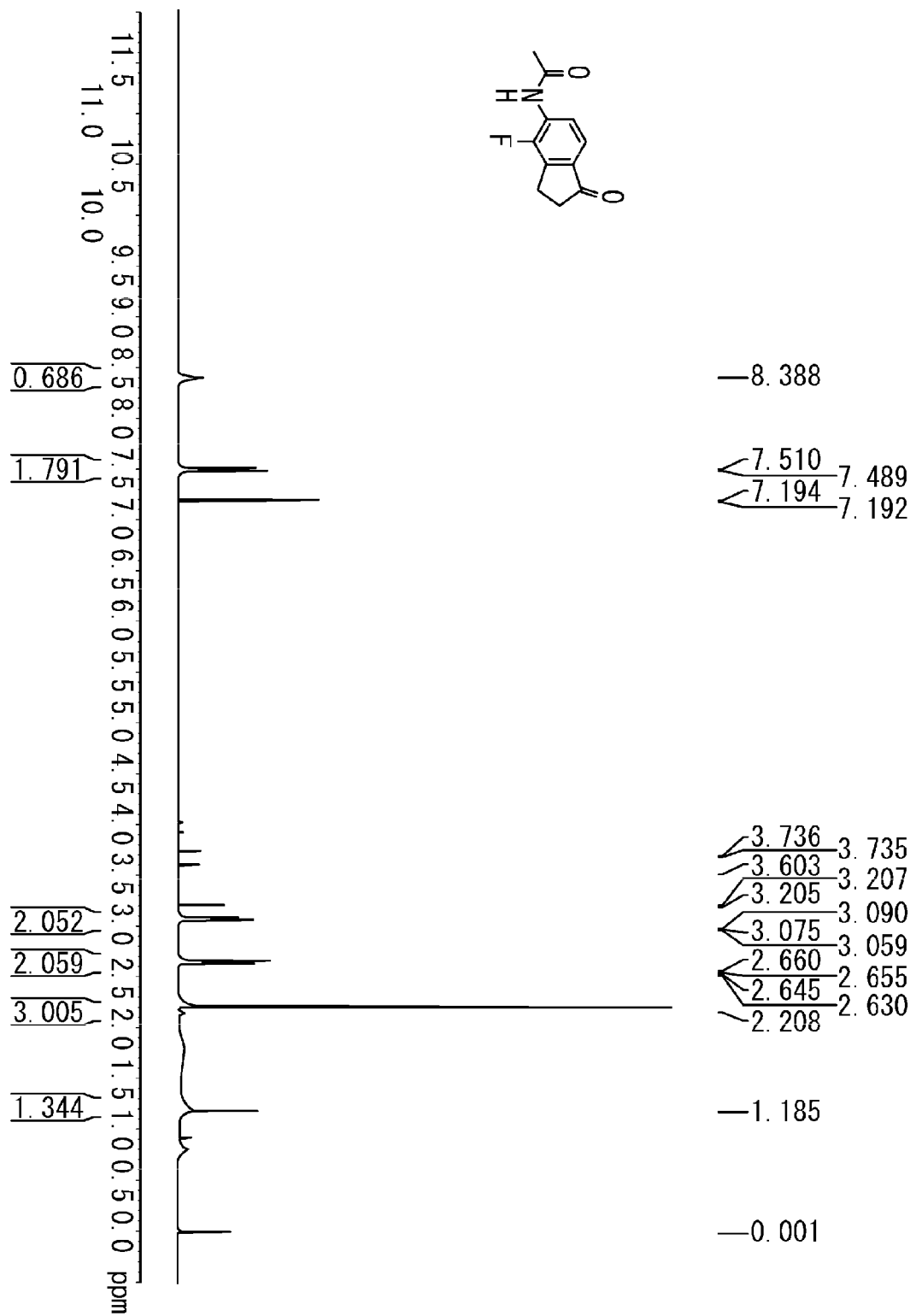
FIG. 6 is a proton nuclear magnetic resonance spectrum of N-(4-fluoro-1-oxo-2,3-dihydro-1H-inden-5-yl)acetamide; i.e., an intermediate of a compound represented by Structural Formula (2), which is one preferred example of a compound represented by General Formula (V)

The N-(4-fluoro-1-oxo-2,3-dihydro-1H-inden-5-yl)acetamide was analyzed through proton nuclear magnetic resonance (NMR) in deuterated chloroform (CDCl$_3$) at 400 MHz and 25° C. The obtained proton nuclear magnetic resonance spectrum is presented in FIG. 6.

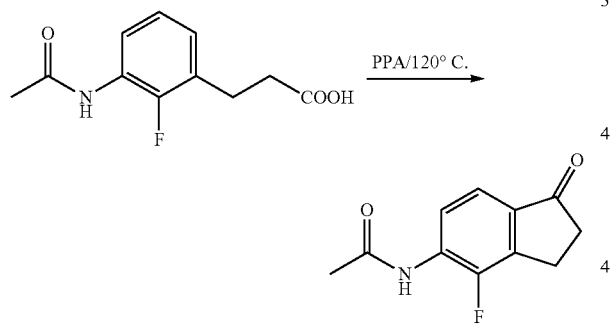

<Preparation of 5-amino-4-fluoro-2,3-dihydro-1H-inden-1-one>

As presented in the following reaction formula, a solution of N-(4-fluoro-1-oxo-2,3-dihydro-1H-inden-5-yl)acetamide (3 g, 0.01 mmol) in concentrated sulfuric acid (20 mL) was stirred at 80° C. for 0.5 hours. The resulting mixture was treated with 4N sodium hydroxide so that the pH thereof was adjusted to 10 to 12, and then extracted three times with 100 mL of ethyl acetate. The combined organic phase was washed with saturated brine (100 mL), and dried and concentrated with anhydrous sodium sulfate, to thereby give 5-amino-4-fluoro-2,3-dihydro-1H-inden-1-one (2.3 g, yield: 96%).

Figure 7:
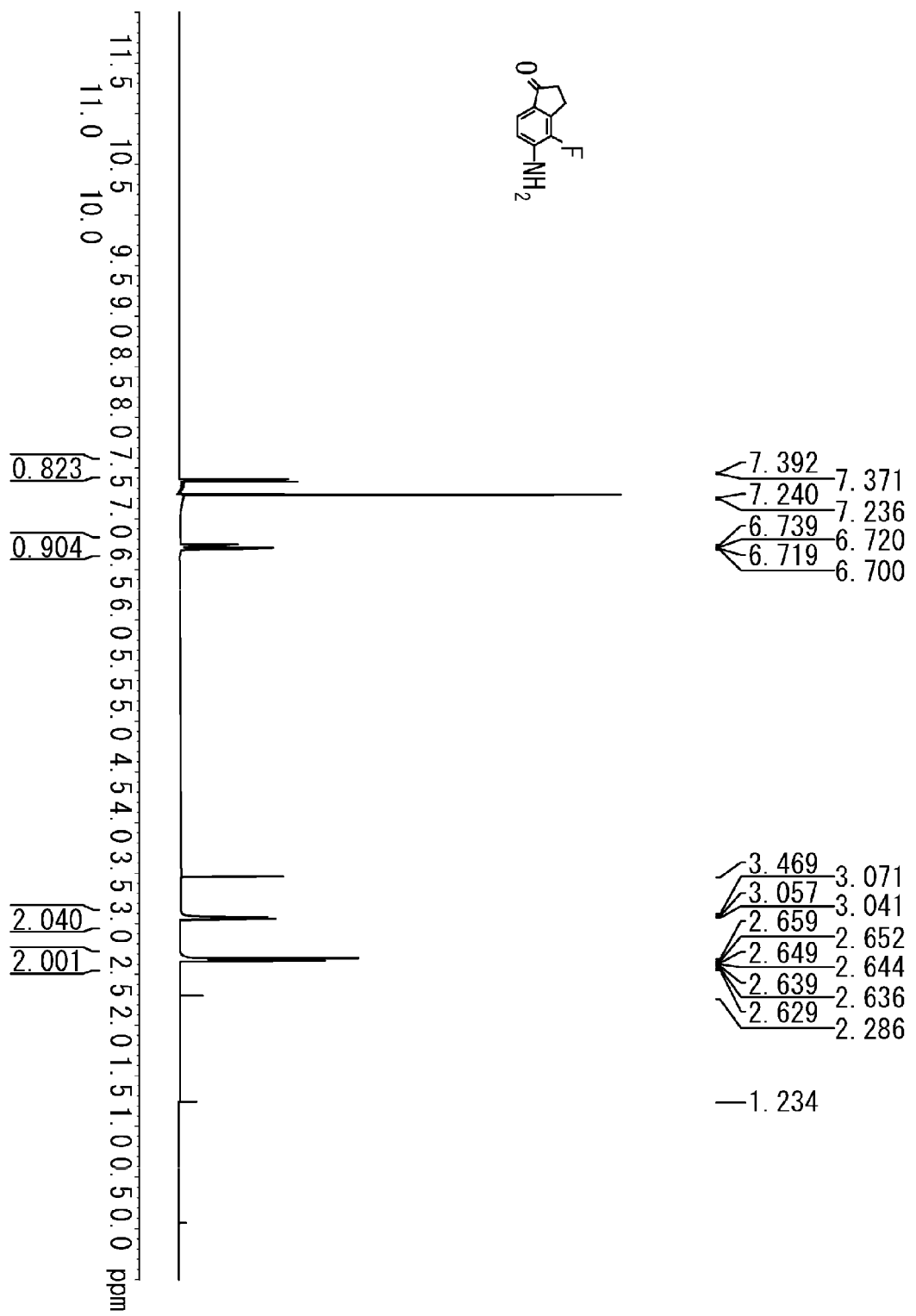
FIG. 7 is a proton nuclear magnetic resonance spectrum of 5-amino-4-fluoro-2,3-dihydro-1H-inden-1-one: i.e., an intermediate of a compound represented by Structural Formula (2), which is one preferred example of a compound represented by General Formula (V)

The 5-amino-4-fluoro-2,3-dihydro-1H-inden-1-one was analyzed through proton nuclear magnetic resonance (NMR) in deuterated chloroform (CDCl$_3$) at 400 MHz and 25° C. The obtained proton nuclear magnetic resonance spectrum is presented in FIG. 7.

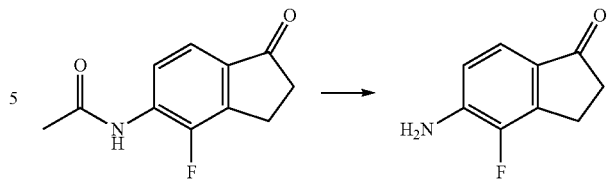

<Preparation of 5-(benzylamino)-4-fluoro-2,3-dihydro-1H-inden-1-one>

As presented in the following reaction formula, a mixture of 5-amino-4-fluoro-2,3-dihydro-1H-inden-1-one (2.3 g, 14 mmol), cesium carbonate (Cs$_2$CO$_3$; 12 g, 28 mmol) and benzyl bromide (0.17 g, 72 mmol) in acetonitrile (CH$_3$CN; 20 mL) was stirred under reflux for 48 hours. The mixture was concentrated to obtain the residue, which was dissolved in water (20 mL). The resulting solution was extracted three times with 20 mL of ethyl acetate. The combined organic phase was washed with saturated brine (50 mL), and dried and concentrated with anhydrous sodium sulfate to thereby give a crude product, which was purified by pre-TLC to give 5-(benzylamino)-4-fluoro-2,3-dihydro-1H-inden-1-one (370 mg, yield: 10%) as a yellow solid.

Figure 8:
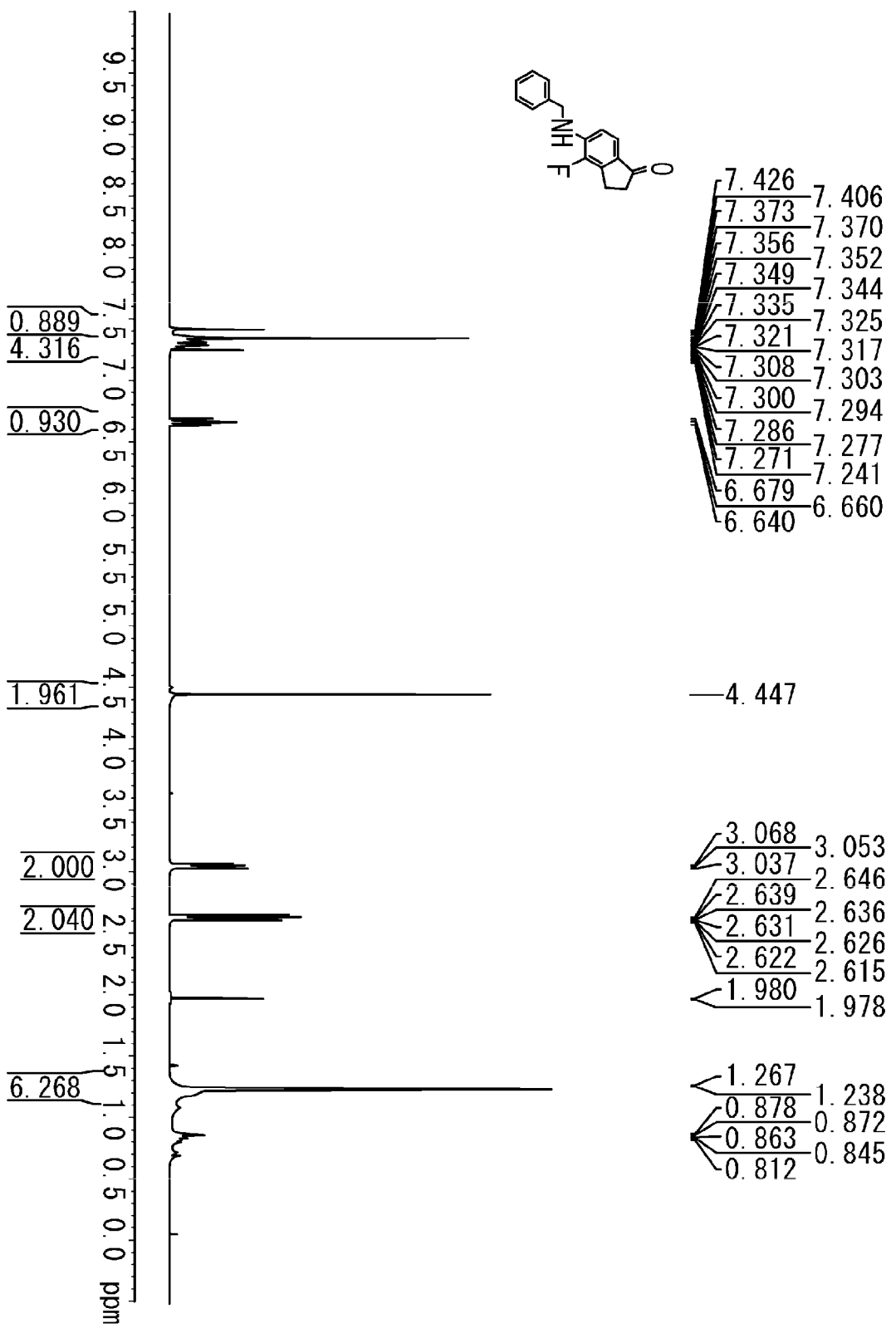
FIG. 8 is a proton nuclear magnetic resonance spectrum of 5-(benzylamino)-4-fluoro-2,3-dihydro-1H-inden-1-one; i.e., an intermediate of a compound represented by Structural Formula (2), which is one preferred example of a compound represented by General Formula (V)

The 5-(benzylamino)-4-fluoro-2,3-dihydro-1H-inden-1-one was analyzed through proton nuclear magnetic resonance (NMR) in deuterated chloroform (CDCl$_3$) at 400 MHz and 25° C. The obtained proton nuclear magnetic resonance spectrum is presented in FIG. 8.

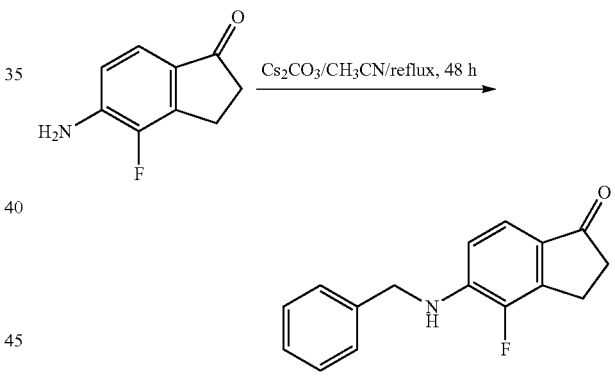

<Preparation of Compound Represented by Structural Formula (2)>

As presented in the following reaction formula, N,N-diethyl-2-iodoacetamide (723 mg, 3 mmol) was added dropwise at room temperature to a mixture of 5-(benzylamino)-4-fluoro-2,3-dihydro-1H-inden-1-one (370 mg, 1.5 mmol) and cesium carbonate (Cs$_2$CO$_3$: 940 mg, 3 mmol) in acetonitrile (CH$_3$CN; 20 mL). Then, the mixture was refluxed for 48 hours. The mixture was filtered and the filtrate was concentrated to give a crude product, which was purified by pre-TLC (product of Merck Co., Ltd.) to give 2-(benzyl(4-fluoro-1-oxo-2,3-dihydro-1H-inden-5-yl)amino)-N,N-diethylacetamide represented by Structural Formula (2) (5 mg, yield: 1%) as a yellow solid.

The 2-(benzyl(4-fluoro-1-oxo-2,3-dihydro-1H-inden-5-yl)amino)-N,N-diethylacetamide was analyzed through proton nuclear magnetic resonance (NMR) in deuterated chloroform (CDCl$_3$) at 400 MHz and 25° C. The obtained proton nuclear magnetic resonance spectrum is presented in FIG. 9.

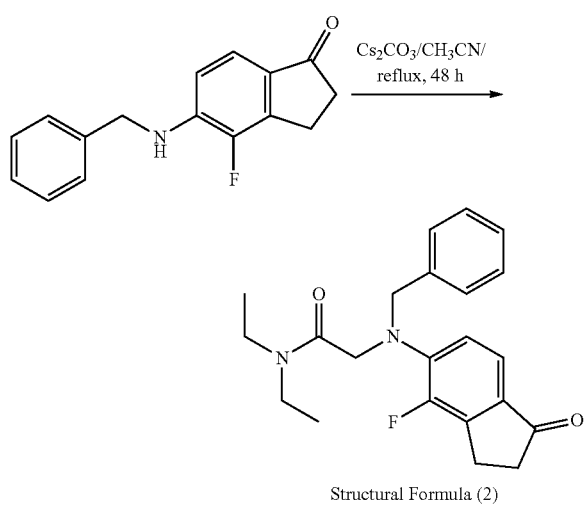

Structural Formula (2)

PRODUCTION EXAMPLE 3

Synthesis of Compounds Represented by Structural Formulas (3) and (4)

<Preparation of 3-phenylbutanoic acid>

As presented in the following reaction formula, n-butyllithium (n-BuLi; 428 mL, 1.07 mol) was added dropwise at −78° C. to −65° C. to a mixture of bromobenzene (166 g, 1.07 mol) in tetrahydrofuran (THF; 500 mL), followed by stirring at −78° C. for 0.5 hours. Then, (E)-but-2-enoic acid (46 g, 0.53 mol) was added dropwise to the resulting mixture. After the completion of reaction, the mixture was treated with hydrochloric acid so that the pH thereof was adjusted to 1.0, and then extracted twice with 500 mL of dichloromethane (DCM). The combined organic phase was dried and concentrated with magnesium sulfate to give a crude product, which was purified by column chromatography (using 300 g of silica gel (product of Merck Co., Ltd.) to give 3-phenylbutanoic acid (52 g, yield: 60%) as a yellow liquid.

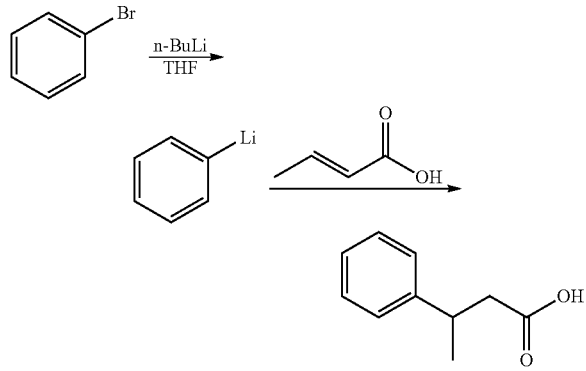

<Preparation of 3-methyl-2,3-dihydro-1H-inden-1-one>

As presented in the following reaction formula, a mixture of 3-phenylbutanoic acid (30 g, 0.18 mol) in thionyl chloride (SOCl$_2$; 100 mL) was refluxed under heating for 2 hours, and then the thionyl chloride was removed. Toluene (200 mL) and aluminum chloride (AlCl$_3$; 24 g, 0.18 mol) were added to the resulting mixture at 0° C., and the reaction mixture was stirred at 0° C. for 0.5 hours, followed by refluxing under heating. After the completion of reaction, the mixture was treated with ice water and then extracted twice with 200 mL of dichloromethane (DCM). The combined organic phase was washed with water (100 mL) and saturated brine (100 mL), and dried and concentrated with magnesium sulfate to give a crude product. The crude product was purified by gel column chromatography (using 100 g of silica gel (product of Merck Co., Ltd.)) using an eluent of pentane (PE):ethyl acetate (20:1 (by volume)) to give 3-methyl-2,3-dihydro-1H-inden-1-one (16 g, yield: 60%) as a brown oil.

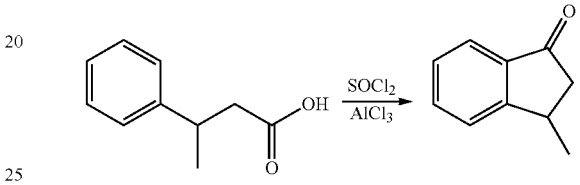

<Preparation of 3-methyl-6-nitro-2,3-dihydro-1-H-inden-1-one>

As presented in the following reaction formula, a solution of potassium nitrate (KNO$_2$; 6.2 g, 0.06 mol) in sulfuric acid (30 mL) was added dropwise at 0° C. to a mixture of 3-methyl-2,3-dihydro-1H-inden-1-one (9.0 g, 0.06 mol) in sulfuric acid ic (H$_2$SO$_4$; 40 mL). Then, the mixture was stirred at 0° C. until the completion of reaction. The mixture obtained after the reaction was added to ice water and filtered. The cake was washed with water and purified by silica gel (100 g) column chromatography (product of Merck Co., Ltd.) using an eluent of pentane (PE):ethyl acetate (10:1 (by volume)) to give 3-methyl-6-nitro-2,3-dihydro-1-H-inden-1-one (8 g, yield: 69%) as a yellow solid.

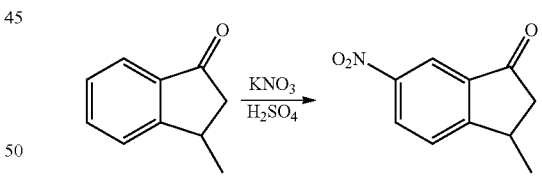

<Preparation of 6-amino-3-methyl-2,3-dihydro-1-H-inden-1-one>

As presented in the following reaction formula, tin chloride (SnCl$_2$; 26.5 g, 0.117 mol) was added at room temperature to a mixture of 3-methyl-6-nitro-2,3-dihydro-1-H-inden-1-one (5.0 g, 0.026 mol), hydrochloric acid (HCl; 90 mL) and water (H$_2$O; 30 mL), and the reaction mixture was stirred at 40° C. for 0.5 hours. After the completion of reaction, the mixture was treated with saturated, anhydrous potassium carbonate (K$_2$CO$_3$; 300 mL) and then extracted three times with 100 mL of dichloromethane. The combined organic phase was concentrated to give 6-amino-3-methyl-2,3-dihydro-1-H-inden-1-one (3.8 g, yield: 92%).

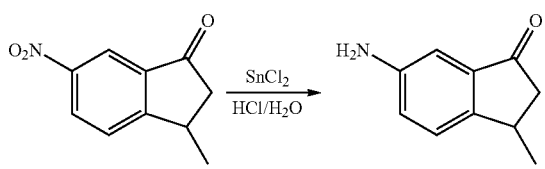

Preparation of N-(1-methyl-3-oxo-indan-5-yl)benzamide>

As presented in the following reaction formula, a solution of benzoyl chloride (PhCOCl; 6.7 g, 0.043 mol) in dichloromethane (DCM; 20 mL) was added at 0° C. to a mixture of 3-methyl-6-nitro-2,3-dihydro-1-H-inden-1-one (7 g, 0.043 mol) and triethylamine (9.6 g, 0.095 mol) in dichloromethane (DCM; 100 mL), and the reaction mixture was stirred for 2 hours. After the completion of reaction, the mixture was washed with water (50 mL), saturated sodium hydrogen carbonate (50 mL) and saturated brine (50 mL) and then concentrated to give a crude product. The crude product was purified by silica gel (50 g) column chromatography (product of Merck Co., Ltd.) using an eluent of pentane (PE):ethyl acetate (10:1 (by volume)) to give the desired product N-(1-methyl-3-oxo-indan-5-yl)benzamide (10 g, yield: 87%) as a yellow solid.

<Preparation of [benzyl-(1-methyl-3-oxo-indan-5-yl-amino]-acetic acid ethyl ester>

As presented in the following reaction formula, a solution of bromoethyl acetate (BrCH₂COOEt; 7.5 g, 0.045 mol) in acetonitrile (20 mL) was added to a mixture of N-(1-methyl-3-oxo-indan-5-yl)benzamide (10 g, 0.037 mol) and anhydrous potassium carbonate (10.4 g, 0.075 mol) in acetonitrile (150 mL), and the reaction mixture was refluxed for 5 hours. After the completion of reaction, the mixture was filtered and the filtrate was concentrated to give the crude product [benzyl-(1-methyl-3-oxo-indan-5-yl)-amino]-acetic acid ethyl ester (8 g, yield: 63%) as a yellow solid.

<Preparation of [benzyl-(3-hydroxy-1-methyl-indan-5-yl)-amino]-acetic acid ethyl>ester As presented in the following reaction formula, a mixture of boran (BH₃) in methyl sulfide (Me₂S; 1.4 mL, 0.014 mol) was added to a solution of [benzyl-(1-methyl-3-oxo-indan-5-yl)-amino]-acetic acid ethyl ester (4 g, 0.011 mol) and tetrahydrofuran (THF; 50 mL), and the reaction mixture was refluxed for 2 hours. The mixture of BH₃ in Me₂S (1.4 mL, 0.014 mol) was added several times in a divided manner until there was no reactant left. The reaction was terminated with methanol (10 mL) at 0° C. The resulting mixture was heated to room temperature and stirred for 0.5 hours. The mixture was concentrated to give a crude product. The crude product was purified by silica gel (30 g) column chromatography (product of Merck Co., Ltd.) using an eluent of pentane (PE):ethyl acetate (5:1 (by volume)) to give the desired product [benzyl-(3-hydroxy-1-methyl-indan-5-yl)-amino]-acetic acid ethyl ester (1.4 g, yield: 32%).

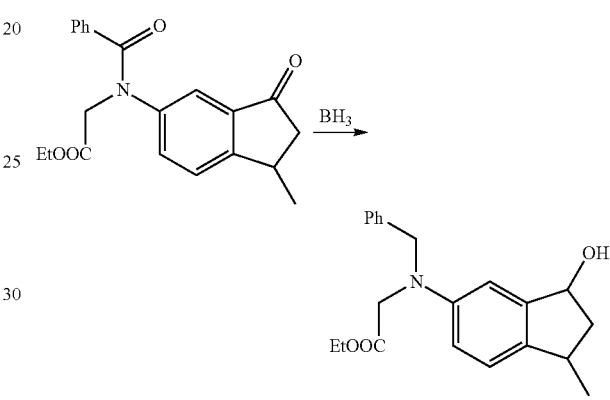

<Preparation of [benzyl-(3-hydroxy-1-H-indan-5-yl)-amino]-acetic acid ethyl ester>

As presented in the following reaction formula, a mixture of [benzyl-(3-hydroxy-1-methyl-indan-5-yl)-amino]-acetic acid ethyl ester (2 g, 5.9 mmol) and p-toluenesulfonic acid monohydrate (P-TsOH.2H₂O; 0.12 g, 0.6 mmol) in toluene (50 mL) was refluxed for 2 hours. After the completion of reaction, the mixture treated with sodium hydrogen carbonate and then extracted twice with 20 mL of ethyl acetate. The combined organic phase was washed with water (20 mL) and saturated brine (20 mL), and dried and concentrated with magnesium sulfate to give the crude product [benzyl-(3-hydroxy-1-H-indan-5-yl)-amino]-acetic acid ethyl ester (1.5 g, yield: 77%). The crude product was purified with prep-HPLC (product of Waters Co., Ltd.) to give a pure product.

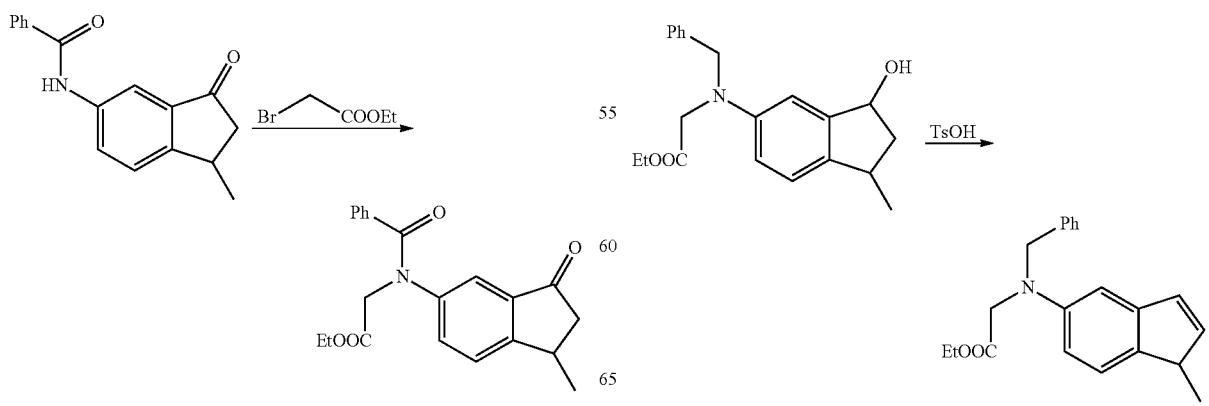

<Preparation of [benzyl-(3-hydroxy-1-H-indan-5-yl)-amino]-acetic acid>

As presented in the following reaction formula, a mixture of [benzyl-(3-hydroxy-1-H-indan-5-yl)-amino]-acetic acid ethyl ester (0.5 g, 0.0016 mol), lithium hydroxide (LiOH; 0.13 g, 0.003 mol), tetrahydrofuran (THF; 7 mL), water (3 mL) and methanol (3 mL) was stirred at room temperature until the completion of reaction. The resulting mixture was treated with hydrochloric acid so that the pH thereof was adjusted to 6.0, and then extracted with 30 mL of dichloromethane. The combined organic phase was washed with saturated brine (25 mL) and dried and concentrated with magnesium sulfate to give the crude product [benzyl-(3-hydroxy-1-H-indan-5-yl)-amino]-acetic acid (0.32 g, 70%). The crude product was used for the next step without further purification.

Figure 10:
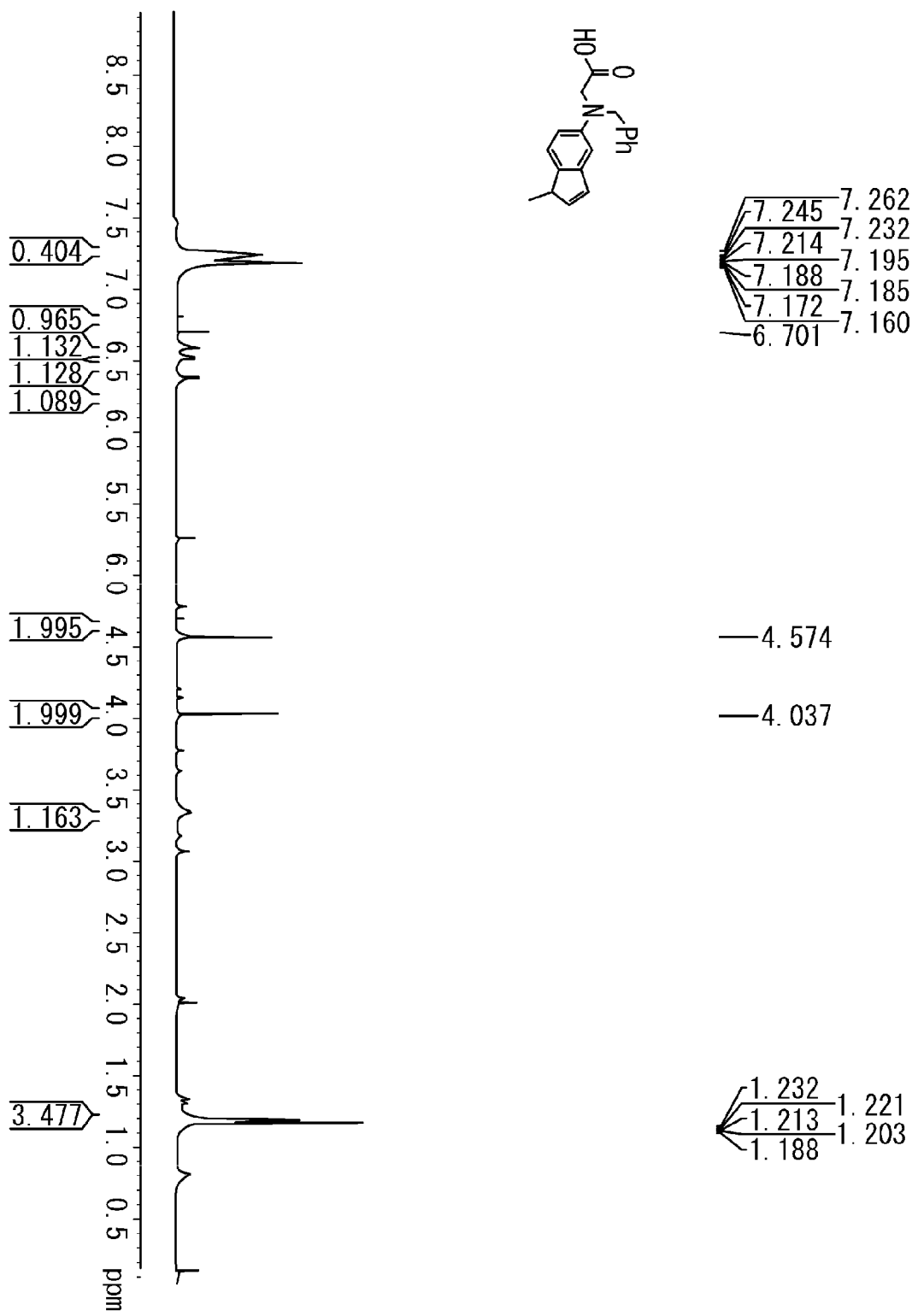
FIG. 10 is a proton nuclear magnetic resonance spectrum of [benzyl-(3-hydroxy-1-H-indan-5-yl)-amino]-acetic acid; i.e., an intermediate of a compound represented by Structural Formula (2), which is one preferred example of a compound represented by General Formula (VI)

The [benzyl-(3-hydroxy-1-H-indan-5-yl)-amino]-acetic acid was analyzed through proton nuclear magnetic resonance (NMR) in deuterated chloroform (CDCl$_3$) at 400 MHz and 25° C. The obtained proton nuclear magnetic resonance spectrum is presented in FIG. 10.

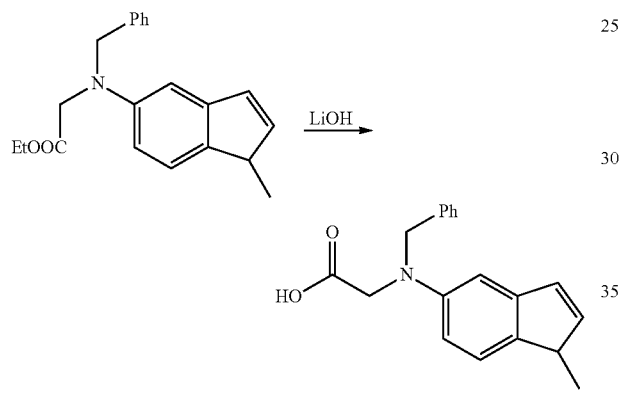

<Preparation of Compounds Represented by Structural Formulas (3) and (4)>

As presented in the following reaction formula, amine (3.5 mmol) was added at 20° C. for 1 hour to a mixture of [benzyl-(3-hydroxy-1-H-indan-5-yl)-amino]-acetic acid (0.2 g, 0.7 mmol), HATU (0.38 g, 1 mmol, product of Aldrich Co., Ltd.), triethylamine (Net$_3$; 0.5 g, 5 mmol) and dichloromethane (10 mL). Then, the mixture was washed three times with 20 mL of water and purified by prep-HPLC (product of Waters Co., Ltd.) to give a compound represented by Structural Formula (3) (42 mg, yield: 19%) and a compound represented by Structural Formula (4) (35 mg, yield: 14%).

Although a compound represented by the following Structural Formula (5) (55 mg, yield: 24%) and a compound represented by the following Structural Formula (6) (39 mg, yield: 17%) were obtained, a test in Example 1 described below was performed using the compounds represented by Structural Formulas (3) and (4).

The compounds represented by Structural Formulas (3) and (4) were analyzed through proton nuclear magnetic resonance (NMR) in deuterated chloroform (CDCl$_3$) at 400 MHz and 25° C. The obtained proton nuclear magnetic resonance spectrum of the compound represented by Structural Formula (3) is presented in FIG. 11. The obtained proton nuclear magnetic resonance spectrum of the compound represented by Structural Formula (4) is presented in FIG. 12.

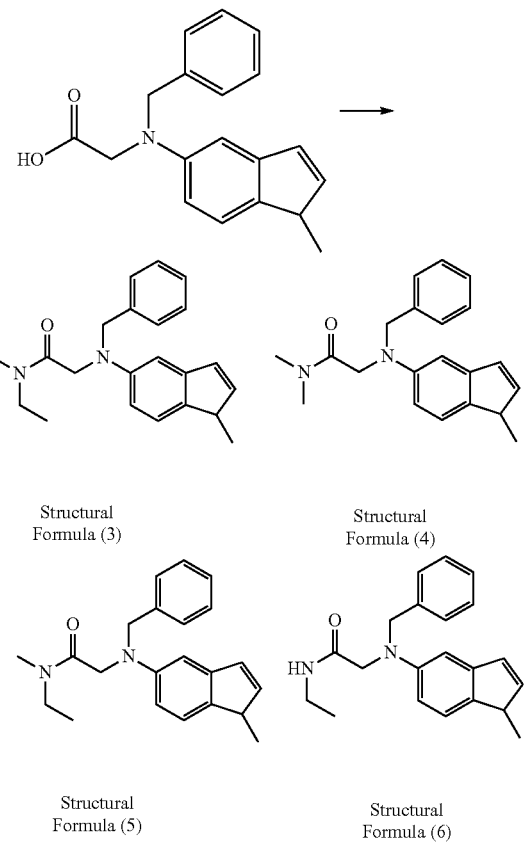

Structural Formula (3)

Structural Formula (4)

Structural Formula (5)

Structural Formula (6)

EXAMPLE 1

Each of the compounds represented by Structural Formulas (1) to (4) was measured for inhibitory activity against a kinesin spindle protein by the following method referring to the methods described in Elizabeth B. Cogan et al., Analytical Biochemistry, 1999, 271, pp. 29-35 and Keith W. Rickert et al., Archives of Biochemistry and Biophysics, 2008, 469, pp. 220-231.

<Preparation of Kinesin Spindle Protein>
—Expression of Kinesin Spindle Protein—

The human KSP motor domain (Uniprot P52732, residues 1-387) was cloned into the pRSETa vector (product of Invitrogen Co., Ltd) and expressed in E. coli BL21 Star (DE3) (product of Invitrogen Co., Ltd) with His6 tag for purification.

Cells of the transformed BL21 Star (DE3) (product of Invitrogen Co., Ltd) were cultured overnight in an LB (Luria-Bertani) medium at 37° C. and 200 rpm. The resulting culture was added to 2 L of an LB medium, and the OD thereof at 600 nm was defined as 0.01. Then, the culture was incubated at 37° C. and 200 rpm until the cell density thereof reached such a density that the OD thereof at 600 nm was 0.4.

The expression of a kinesin spindle protein was induced by addition of 1 mM IPTG (isopropyl-β-D-thiogalactopyranoside). The cells were harvested 3 hours after IPTG induction, and collected by centrifugation at 4° C. and 7,000 g for 15 min. The cells expressing the recombinant kinesin spindle protein were stored as 1 g/pack at −80° C. until use.

—Purification of Kinesin Spindle Protein—

Two grams of the wet cells expressing the recombinant kinesin spindle protein were suspended in 50 mL of an ice cold protein extract buffer (the formulation of which is given below). The cells were treated three times by a microfluidizer (MICROFLUIDIZER, product of Microfluidics Co., Ltd.) at 4° C. and 15,000 psi to lyse the cells. Then, a high performance, high speed, refrigerated centrifuge (Beckman Avanti J-26XP, product of BECKMAN COULTER Co., Ltd.) was used to perform centrifugation at 4° C. and 20,000×g for 30 min, and the resulting supernatant was collected and then filtered with a 0.45 µM filter.

The filtrate was charged to a 1 mL HisTrap (trademark) HP column (product of GE Healthcare Co., Ltd.). His-Buffer A (the formulation of which is given below) and His-Buffer B (the formulation of which is given below) (His-Buffer A:His-Buffer B=95:5 (by volume)) were allowed to flow through the column until the A280 reached the baseline. The recombinant kinesin spindle protein was eluted by allowing His-Buffer B to flow through the column with a linear gradient of 0% by volume to 50% by volume relative to His-Buffer A.

The peak of the kinesin spindle protein was observed at 25% by volume of Buffer B (250 mM imidazole). The fraction (4 mL) of this crude kinesin spindle protein was placed in a dialysis tube (Ting Ke Hong Da (made in China)), and dialyzed against 500 mL of IEX Buffer A (the formulation of which is given below) at 4° C. This dialysis was performed twice.

Further purification was performed through ion exchange (IEX) chromatography. The fraction of the kinesin spindle protein was charged to a 1 mL HisTrap (trademark) SPXL column (product of GE Healthcare Co., Ltd.). IEX Buffer A was allowed to flow through the column until the A280 reached the baseline, and then IEX Buffer A and IEX Buffer B (pH 6.8, the formulations of which are given below) were allowed to flow therethrough with a linear gradient of 0 M to 1 M of sodium chloride.

The kinesin spindle protein was eluted at about 400 mM of sodium chloride and transferred to a storage buffer (the formulation of which is given below) through dialysis. The dialysis was performed by the same method as in the first purification.

The concentration of the finally purified kinesin spindle protein was measured through ultraviolet absorption spectrometry. The concentration of the purified kinesin spindle protein was found to be 1.5 µM. This protein was aliquoted in 100 µL/tube (total amount: 1.45 mL) and stored at −80° C. until use.

[Formulation of Protein Extract Buffer]
 50 mM HEPES (4-(2-hydroxyethyl)-1-piperazineethanesulfonic acid) (pH 8.0)
 2 mM magnesium chloride
 250 mM sodium chloride
 10% by mass glycerol
 0.1% by mass NP-40 (polyoxyethylene(9)octylphenyl ether)
 1 mM dithiothreitol (DTT)
 1 mM phenylmethylsulfonyl fluoride (PMSF)
 0.5 mM ATP-Mg
 10 mM imidazole
 2 mM benzimidine
[Formulation of His-Buffer A]
 50 mM HEPES (pH 8.0)
 2 mM magnesium chloride
 250 mM sodium chloride
 10% by mass glycerol
[Formulation of His-Buffer B]
 50 mM HEPES (pH 8.0)
 2 mM magnesium chloride
 250 mM sodium chloride
 10% by mass glycerol
 1 M imidazole
[Formulation of IEX Buffer A]
 50 mM HEPES (pH 6.8)
 1 mM magnesium chloride
 1 mM dithiothreitol (DTT)
 10% by mass glycerol
[Formulation of IEX Buffer B]
 50 mM HEPES (pH 6.8)
 1 mM magnesium chloride
 1 mM dithiothreitol (DTT)
 10% by mass glycerol
 1 M sodium chloride
[Storage Buffer]
 50 mM HEPES (pH 6.8)
 1 mM magnesium chloride
 1 mM dithiothreitol (DTT)
 10% by mass glycerol <Measurement of Inhibitory Activity Against Kinesin Spindle Protein>

—Preparation of the Compounds Represented by Structural Formulas (1) to (4)—

Each of the compounds represented by Structural Formulas (1) to (4) was prepared in 100% by mass DMSO (dimethylsulfoxide) at 100-fold concentration (100×). Then, the resulting mixture was diluted with 1.00% by mass DMSO to each of 0.001 mM, 0.003 mM, 0.01 mM, 0.03 mM, 0.1 mM, 0.3 mM, 1 mM, 3 mM, 10 mM and 30 mM.

—Method for Measuring Inhibitory Activity Against Kinesin Spindle Protein—

A reaction mixture having a formulation described in the following Table 1 was prepared. Specifically, 28.5 µL of water, 1 µL (1.5 M) of the above-purified kinesin spindle protein, 5 µL of a 10× reaction buffer (150 mM PIPES (1,4-piperazine ethanesulfonic acid) (pH 7.0), 10 mM magnesium chloride, 10 mM EGTA (glycol ether diamine tetraacetate)), 10 µL of 5× microtubules solution (330 µg/mL microtubules, 15 mM PIPES (pH 7.0), 1 mM magnesium chloride, 10 µM Taxol) and 0.5 µL of the above-prepared 100× compound (the compound represented by Structural Formula (1), (2), (3) or (4)) were mixed together to prepare 45 µL of a reaction mixture, which was incubated at 37° C. for 10 min. Then, 5 µL of a 100×ATP solution (10 mM ATP, 10 mM PIPES (pH 7.0)) was added to the reaction mixture to initiate the reaction. Immediately after that, the reaction mixture was incubated at 37° C. for 20 min. Note that, the final concentrations of the ingredients in 50 µL of the reaction mixture were 19 mM PIPES, 1 mM EGTA, 1.2 mM magnesium chloride, 2 µM Taxol, 66 µg/mL microtubules, 30 nM kinesin spindle protein and 1 mM ATP.

Also, for a high control, a reaction mixture was prepared in the same manner as described above except that 100% by mass DMSO only was used instead of the 100× compound, and was allowed to react in the same manner as described above.

For a low control, a reaction mixture was prepared in the same manner as described above except that 1 µL of water was added instead of 1 µL of the kinesin spindle protein, and was allowed to react in the same manner as described above.

TABLE 1

| Formulation | Volume (µL) |
| --- | --- |
| Water | 28.5 |
| 10 × Reaction Buffer | 5 |
| 5 × Microtubules | 10 |

TABLE 1-continued

| Formulation | Volume (μL) |
| --- | --- |
| 50 × Kinesin Spindle Protein | 1 |
| 10 × ATP | 5 |
| 100 × Compound | 0.5 |
| Total | 50 |

After the reaction, 150 μL of Quench C buffer (the formulation of which is given below) was added the reaction mixture to terminate the reaction, followed by incubating at room temperature for 5 min. Then, the reaction mixture was measured for absorbance at 525 nm with a microplate reader (SpectraMax, product of Molecular Devices Co., Ltd.).
[Formulation of Quench C]
100 μL of Quench A (1 mg/mL quinaldine red (QR), 0.14% by mass PVA) and 50 μL of Quench B (1.15 M sulfuric acid, 12.3 mM ammonium heptamolybdate) were mixed together. Note that, fresh Quench C buffer was prepared before each test.

The kinesin spindle protein decomposes ATP into ADP and Pi (phosphoric acid). The Pi formed after decomposition binds to quinaldine red (QR) and ammonium heptamolybdate to form a complex. Thus, the amount of the formed Pi can be measured by measuring the absorbance at 525 nm. With the absorbance at 525 nm of the high control (the amount of the formed Pi) being 100, comparing the absorbance of the high control with absorbance of test groups to which the above compounds have been added can determine whether the activity of the kinesin spindle protein is inhibited.

That is, the inhibitory rate of the activity of the kinesin spindle protein can be calculated from the following calculation formula. The following Table 2 presents relationships between the concentrations of each of the compounds and the inhibitory rate of the activity of the kinesin spindle protein.

Inhibitory rate(%)=$(S-L)/(H-L)\times 100$

In the above calculation formula, "S" denotes absorbance of the tested reaction mixture containing the compound represented by Structural Formula (1), (2), (3) or (4), "L" denotes absorbance of the low control, and "H" denotes absorbance of the high control.

TABLE 2

| Compounds | Concentration (μM) | Inhibitory rate (%) |
| --- | --- | --- |
| Compound represented by Structural Formula (1) | 10 | 44.5 |
| Compound represented by Structural Formula (2) | 88 | 50 |
| Compound represented by Structural Formula (3) | 39 | 50 |
| Compound represented by Structural Formula (4) | 100 | 79.8 |

As is clear from Table 2, each of the compounds represented by Structural Formulas (1), (2), (3) and (4) was found to suitably inhibit the activity of the kinesin spindle protein.

All examples and conditional language provided herein are intended for pedagogical purposes to aid the reader in understanding the invention and the concepts contributed by the inventor to further the art, and are not to be construed as limitations to such specifically recited examples and conditions, nor does the organization of such examples in the specification related to a showing of the superiority and inferiority of the invention. Although one or more embodiments of the present invention have been described in detail, it should be understood that the various changes, substitutions, and alterations could be made hereto without departing from the spirit and scope of the invention.

The invention claimed is:

1. A compound represented by the following General Formula (I):

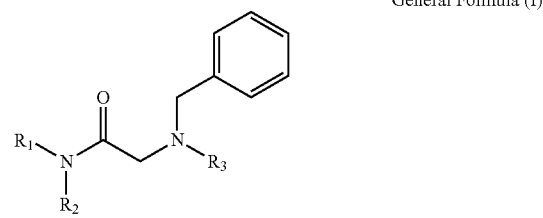

General Formula (I)

where, in General Formula (I), $R_1$ and $R_2$ each represent an alkyl group which may have a substituent, $R_3$ represents the following General Formula (II) or (III), and $R_1$ and $R_2$ may be identical or different,

General Formula (II)

General Formula (III)

where, in General Formulas (II) and (III),

X represents a hydrogen atom or a halogen atom, $R_4$ represents a methyl group, a dimethyl group or an oxygen atom, and

* represents a binding position.

2. The compound according to claim 1, wherein the compound represented by General Formula (I) is a compound represented by the following General Formula (IV), (V) or (VI):

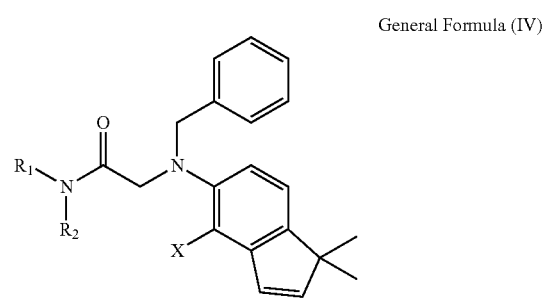

General Formula (IV)

General Formula (V)

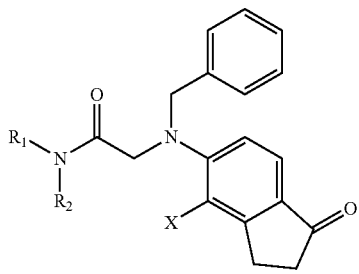

General Formula (VI)

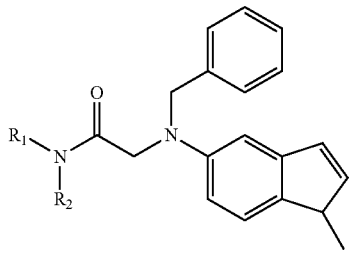

where, in General Formulas (IV), (V) and (VI),

R₁ and R₂ each represent an alkyl group which may have a substituent,

X represents a hydrogen atom or a halogen atom, and

R₁ and R₂ may be identical or different.

3. The compound according to claim 1, wherein in the compound represented by General Formula (I), R₁ or R₂ is or both R₁ and R₂ are an ethyl group or a methyl group, and X represents a hydrogen atom, a fluorine atom or a chlorine atom.

4. The compound according to claim 1, wherein the compound represented by General Formula (I) is a compound represented by the following Structural Formula (1), (2), (3) or (4):

Structural Formula (1)

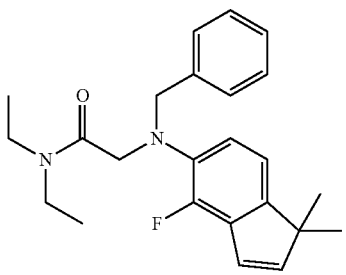

Structural Formula (2)

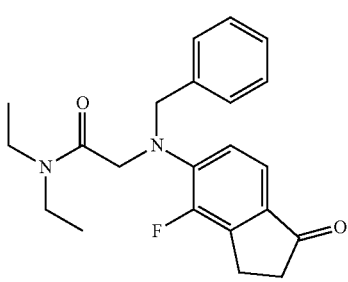

Structural Formula (3)

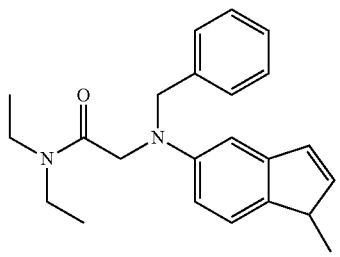

Structural Formula (4)

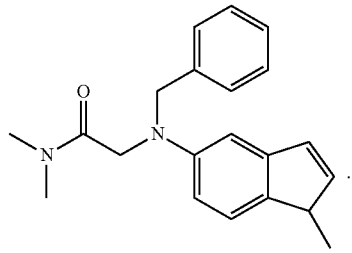

5. A kinesin spindle protein inhibitor, comprising:

a compound represented by the following General Formula (I), wherein the kinesin spindle protein inhibitor inhibits activity of a kinesin spindle protein, General Formula (I)

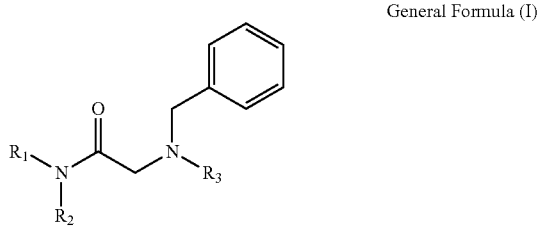

where, in General Formula (I),

R₁ and R₂ each represent an alkyl group which may have a substituent,

R₃ represents the following General Formula (II) or (III), and

R₁ and R₂ may be identical or different,

General Formula (II)

General Formula (III)

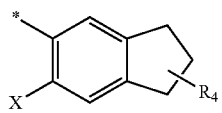

where, in General Formulas (II) and (III),

X represents a hydrogen atom or a halogen atom,

R₄ represents a methyl group, a dimethyl group or an oxygen atom, and

* represents a binding position.

6. A pharmaceutical composition, comprising:
a kinesin spindle protein inhibitor,
wherein the kinesin spindle protein inhibitor comprises a compound represented by the following General Formula (I),
wherein the kinesin spindle protein inhibitor inhibits activity of a kinesin spindle protein, and
wherein the pharmaceutical composition inhibits or treats a disorder mediated at least partially by the kinesin spindle protein, General Formula (I)

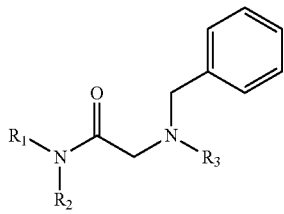

where, in General Formula (I),
$R_1$ and $R_2$ each represent an alkyl group which may have a substituent,
$R_3$ represents the following General Formula (II) or (III), and
$R_1$ and $R_2$ may be identical or different, General Formula (II)

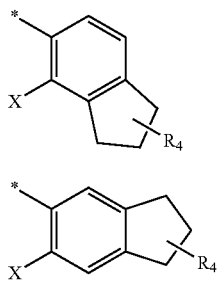

General Formula (III)

where, in General Formulas (II) and (III),
X represents a hydrogen atom or a halogen atom,
$R_4$ represents a methyl group, a dimethyl group or an oxygen atom, and
* represents a binding position.

7. The pharmaceutical composition according to claim 6, wherein the disorder mediated at least partially by the kinesin spindle protein is a cell proliferative disease.

8. The pharmaceutical composition according to claim 6, wherein the disorder mediated at least partially by the kinesin spindle protein is a cell proliferative disease, and
wherein the cell proliferative disease is a cancerous disease.

9. The pharmaceutical composition according to claim 6, wherein the disorder mediated at least partially by the kinesin spindle protein is a cell proliferative disease,
wherein the cell proliferative disease is a cancerous disease, and
wherein the cancerous disease is lung cancer, bronchial cancer, prostate cancer, breast cancer, pancreas cancer, colon cancer, rectal cancer, small intestinal cancer, thyroid cancer, esophageal cancer, oral cancer, pharyngeal cancer, larynx cancer, stomach cancer, liver cancer, intrahepatic bile duct cancer, kidney cancer, renal pelvis cancer, bladder cancer, uterine corpus cancer, uterocervical cancer, ovary cancer, conjunctival cancer, lacrimal cancer, palpebral cancer, multiple myeloma, brain tumor, non-Hodgkin's lymphoma, melanoma, trophoblastic colon adenoma, acute myelocytic leukemia, chronic myelocytic leukemia, lymphatic leukemia, myelocytic leukemia, or any combination thereof.

10. The pharmaceutical composition according to claim 6, further comprising a pharmacologically acceptable carrier.

11. The pharmaceutical composition according to claim 6, further comprising at least one drug used for inhibition or treatment of cancer.

12. A method for inhibiting a kinesin spindle protein, the method comprising:
bringing a kinesin spindle protein inhibitor and cells into contact with each other to inhibit activity of a kinesin spindle protein in the cells,
wherein the kinesin spindle protein inhibitor comprises a compound represented by the following General Formula (I), and
wherein the kinesin spindle protein inhibitor inhibits activity of the kinesin spindle protein, General Formula (I)

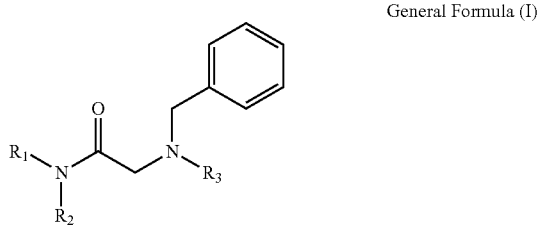

where, in General Formula (I),
$R_1$ and $R_2$ each represent an alkyl group which may have a substituent,
$R_3$ represents the following General Formula (II) or (III), and
$R_1$ and $R_2$ may be identical or different, General Formula (II)

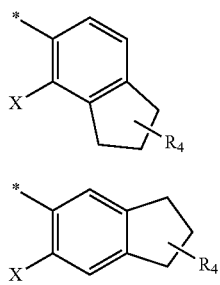

General Formula (III)

where, in General Formulas (II) and (III),
X represents a hydrogen atom or a halogen atom,
$R_4$ represents a methyl group, a dimethyl group or an oxygen atom, and
* represents a binding position.

13. The method according to claim 12,
wherein the cells are cells in vivo or cultured cells.

14. The method according to claim 12,
wherein the cells are cells in vivo or cultured cells, and
wherein the kinesin spindle protein inhibitor is administered to an animal to bring the kinesin spindle protein inhibitor and the cells in vivo into contact with each other.

15. The method according to claim 12,
wherein the cells are cells in vivo or cultured cells,
wherein the kinesin spindle protein inhibitor is administered to an animal to bring the kinesin spindle protein inhibitor and the cells in vivo into contact with each other, and
wherein the animal is human.

16. An inhibiting or treating method, comprising:
inhibiting or treating a disorder mediated at least partially by a kinesin spindle protein using a pharmaceutical composition,
wherein the pharmaceutical composition comprises a kinesin spindle protein inhibitor,
wherein the kinesin spindle protein inhibitor comprises a compound represented by the following General Formula (I),
wherein the kinesin spindle protein inhibitor inhibits activity of a kinesin spindle protein, and
wherein the pharmaceutical composition inhibits or treats a disorder mediated at least partially by the kinesin spindle protein,

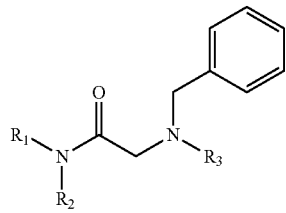

General Formula (I)

where, in General Formula (I),
$R_1$ and $R_2$ each represent an alkyl group which may have a substituent,
$R_3$ represents the following General Formula (II) or (III), and
$R_1$ and $R_2$ may be identical or different,

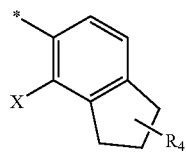

General Formula (II)

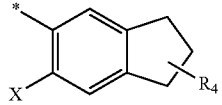

General Formula (III)

where, in General Formulas (II) and (III),
X represents a hydrogen atom or a halogen atom,
$R_4$ represents a methyl group, a dimethyl group or an oxygen atom, and
* represents a binding position.

17. The inhibiting or treating method according to claim 16,
wherein the disorder mediated at least partially by the kinesin spindle protein is a cell proliferative disease.

18. The inhibiting or treating method according to claim 16,
wherein the disorder mediated at least partially by the kinesin spindle protein is a cell proliferative disease, and
wherein the cell proliferative disease is a cancerous disease.

19. The inhibiting or treating method according to claim 16,
wherein the disorder mediated at least partially by the kinesin spindle protein is a cell proliferative disease,
wherein the cell proliferative disease is a cancerous disease, and
wherein the cancerous disease is lung cancer, bronchial cancer, prostate cancer, breast cancer, pancreas cancer, colon cancer, rectal cancer, small intestinal cancer, thyroid cancer, esophageal cancer, oral cancer, pharyngeal cancer, larynx cancer, stomach cancer, liver cancer, intrahepatic bile duct cancer, kidney cancer, renal pelvis cancer, bladder cancer, uterine corpus cancer, uterocervical cancer, ovary cancer, conjunctival cancer, lacrimal cancer, palpebral cancer, multiple myeloma, brain tumor, non-Hodgkin's lymphoma, melanoma, trophoblastic colon adenoma, acute myelocytic leukemia, chronic myelocytic leukemia, lymphatic leukemia, myelocytic leukemia, or any combination thereof.

20. The inhibiting or treating method according to claim 16,
wherein the inhibiting or treating a disorder mediated at least partially by the kinesin spindle protein is performed by administering the pharmaceutical composition to an animal.

* * * * *